(12) United States Patent
Hancock et al.

(10) Patent No.: US 8,574,227 B2
(45) Date of Patent: Nov. 5, 2013

(54) TISSUE MEASUREMENT AND ABLATION ANTENNA

(75) Inventors: Christopher Paul Hancock, Bristol (GB); Malcolm White, Coleford (GB)

(73) Assignee: Medical Device Innovations Limited, Halton, Cheshire (GB)

( * ) Notice: Subject to any disclaimer, the term of this patent is extended or adjusted under 35 U.S.C. 154(b) by 854 days.

(21) Appl. No.: 12/523,208

(22) PCT Filed: Oct. 9, 2007

(86) PCT No.: PCT/GB2007/003822
§ 371 (c)(1),
(2), (4) Date: May 5, 2010

(87) PCT Pub. No.: WO2008/043997
PCT Pub. Date: Apr. 17, 2008

(65) Prior Publication Data
US 2010/0228244 A1    Sep. 9, 2010

(30) Foreign Application Priority Data

Oct. 10, 2006 (GB) .................................. 0620058.8

(51) Int. Cl.
*A61B 18/18* (2006.01)
(52) U.S. Cl.
USPC ............................................. 606/33; 606/32
(58) Field of Classification Search
USPC ...................................................... 606/32–45
See application file for complete search history.

(56) References Cited

U.S. PATENT DOCUMENTS 6,223,086 B1    4/2001 Carl et al.
2003/0100894 A1    5/2003 Mahon et al.

FOREIGN PATENT DOCUMENTS

WO    WO 2004/047659 A2    6/2004
WO    WO 2005/115235 A1    12/2005

OTHER PUBLICATIONS

"Dielectric Properties of Body Tissues", Institute for Applied Physics, 2010.

*Primary Examiner* — Linda Dvorak
*Assistant Examiner* — Amanda Scott
(74) *Attorney, Agent, or Firm* — Arent Fox LLP

(57) ABSTRACT

A surgical antenna for radiating microwave energy (e.g. frequency 500 MHz to 60 GHz) from a e.g. ceramic insertion tip (60) into biological tissue is disclosed. The tip is provided at the end of an elongate body which delivers the microwave energy to the tip via an inner conductor (30), an outer conductor (20) surrounding the inner conductor and a dielectric material (50) therebetween. The impedance of the insertion tip (60) is selected to improve impedance matching with the complex conjugate of the complex impedance of the tissue at a treatment frequency. For example the insertion tip may act as or include at least one quarter wavelength impedance transformer. By closely matching the antenna's impedance to the tissue, dynamic tuning (if used) can be performed much more efficiently. Impedance matching at the tip can also focus the radiated energy distribution.

22 Claims, 19 Drawing Sheets

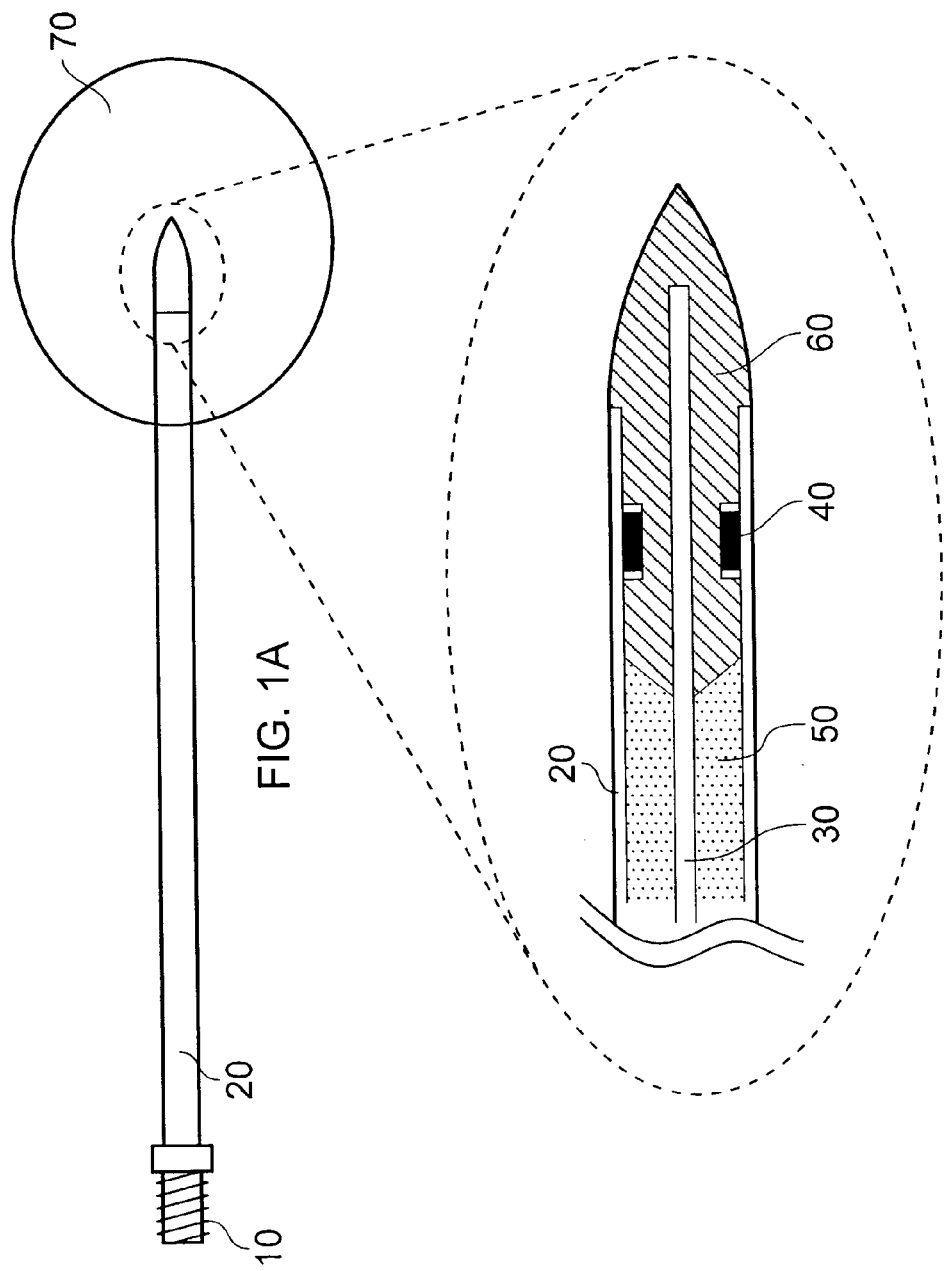

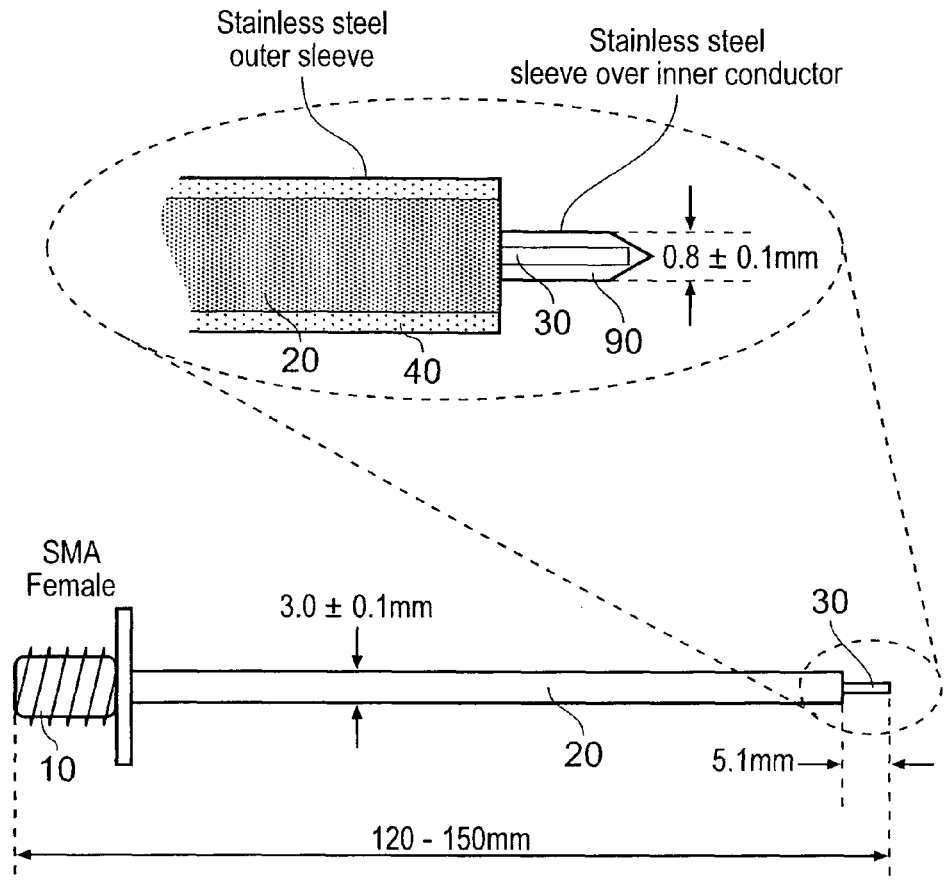
FIG. 17A
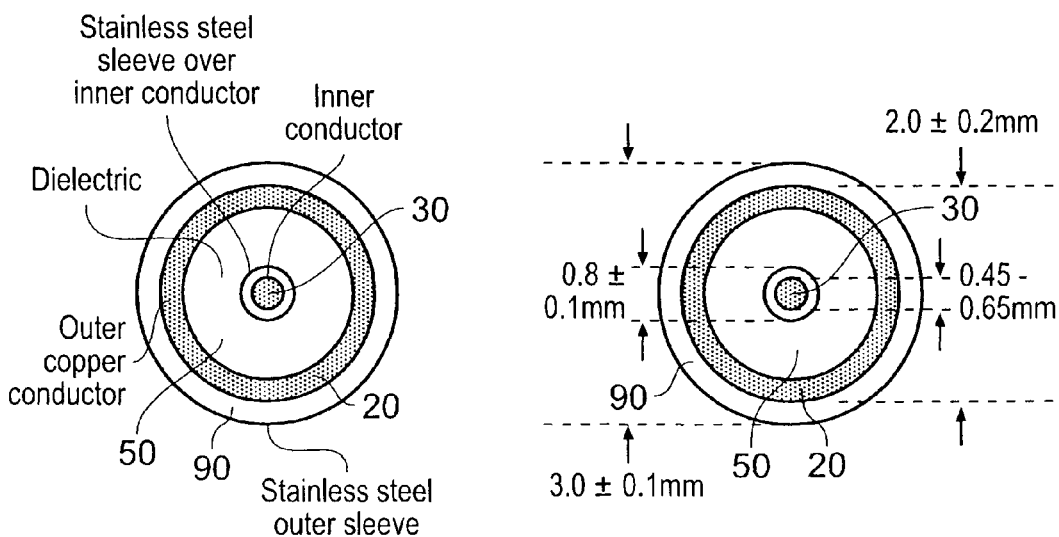
FIG. 17B
FIG. 17C

TISSUE MEASUREMENT AND ABLATION ANTENNA

CROSS-REFERENCE TO RELATED APPLICATION

This application is a National Stage entry of International Application No. PCT/GB2007/003822, having international filing date of Oct. 9, 2007, which claims priority to GB 0620058.8 filed Oct. 10, 2006, the disclosure of each of which is hereby incorporated in its entirety by reference.

TECHNICAL FIELD

The present invention relates to a surgical antenna for delivering microwave energy into biological tissue. For example, surgical antennas are used to perform controlled and focussed ablation of cancerous tumours. Alternatively or additionally, such antennas can measure information concerning the structure of biological tissue e.g. in order to differentiate between tissue types, and/or to identify various types of cancerous tumours, and/or to differentiate between healthy tissue and cancerous tissue, and/or to determine the stage of tumour growth, and/or to provide information to control associated electronic instrumentation to enable the distal end of the antenna to be impedance matched with the complex impedance of the biological tissue in order to enable maximum power transfer between an energy source (or the distal tip of the antenna) and the biological tissue being treated.

BACKGROUND TO THE INVENTION

WO 2004/047659 and WO 2005/115235 relate to apparatus for generating microwave energy suitable for enabling controllable ablation of cancerous tissue using dynamic impedance matching and for making tissue state measurements. In practice, for the controlled ablation/tissue state measurement system to operate efficiently it is desirable to perform dynamic impedance (or energy) matching with the changing tissue load during the process of ablation and measurement of small changes in complex impedance to enable characterisation of various tissue types, tissue states and/or stages associated with the growth of cancerous tumours to be measured.

Conventional antenna structures can be inefficient when used with such systems.

SUMMARY OF THE INVENTION

The present invention may provide an antenna that can contribute to the impedance matching of the electrosurgical systems described in WO 2004/047659 and WO 2005/115235, and that can preferably operate efficiently in both the treatment and measurement modes of operation. However, the present invention need not be limited to use in such systems. It could also be used in other electrosurgical treatment and/or measurement systems.

At its most general, the present invention proposes a surgical antenna, e.g. for use with a dynamic tuning system or mechanism, where the impedance of the distal (insertion) tip of the antenna is selected to enable improved impedance matching with the complex conjugate of the complex impedance of the treatment tissue. In other words, the antenna is designed to impedance match with a representative impedance of a tumour at the frequency of interest e.g. to reduce the effect of standing waves set up in the transmission line structure between the energy source and the antenna due to reflected power travelling back along the transmission line when the antenna is used e.g. in a controlled ablation mode when the tip is in contact with a tumour. By more closely matching the antenna's impedance to the tissue to be ablated or measured, dynamic tuning (if used) can be performed much more efficiently. Moreover, impedance matching the distal tip can focus the energy distribution in this area, thereby providing better energy targeting than conventional antennas.

In this specification microwave means the frequency range of between 500 MHz and 60 GHz, preferably between 5 GHz and 60 GHz, and more preferably between 14 GHz and 15 GHz, and even more preferably a spot frequency of 14.5 GHz.

According to the invention, there may be provided a surgical antenna for insertion into tissue, the antenna comprising an elongate body with an inner conductor along its length, an outer conductor surrounding the inner conductor and separated therefrom by a dielectric material, a connector for connecting the conductors to a microwave power source to receive microwave frequency energy therefrom, and an insertion tip at a distal end of the elongate body for penetrating the tissue, wherein the impedance of the insertion tip is selected to be different from a proximal end of the antenna to provide an impedance, match between the tissue and the proximal end of the antenna. In other words, the antenna comprises two or more longitudinal sections having differing impedances selected to improve impedance matching e.g. between the microwave power source and tissue to be treated.

Preferably, the outer conductor is coaxial with the inner conductor. The outer conductor is preferably cylindrical. The insertion tip may be formed from the inner conductor, e.g. the inner conductor may protrude at the distal end of the antenna. It may be coated where it protrudes to adjust its impedance. Preferably, the insertion tip is an independent piece of dielectric material (preferably different from the dielectric material that separates the inner and outer conductors, more preferably ceramic) that is attached at the distal end of the antenna. The tip dielectric material may act as a first impedance transformer to match the dielectric material that separates the inner and outer conductors with the tumour. It may be preferable to also include a second impedance transformer. The second transformer may be an additional dielectric material or a metallic material that may be used as a fixed tuning stub to introduce inductive reactance for matching with unwanted capacitive or inductive reactance that may be present in the structure. The inner conductor may extend further than the outer conductor at the distal end, e.g. into the separate insertion tip.

The insertion tip is preferably shaped to be insertable inside various regions of the human anatomy with a minimal amount of force; the arrangement has been developed to cause a minimal amount of patient discomfort during the insertion produce and to produce a minimal amount of short term scarring when removed at the end of the treatment/measurement procedure.

Preferably, the antenna is adapted for treating spherical breast tumours with diameters of up to around 2 cm, and for measuring information relating to the characteristics of the biological tissue as the antenna is inserted through various layers of biological tissue relating to the structure of the breast and the tumour contained within. However, the antenna disclosed here is not necessarily limited to being used in this specific application. For example, the antenna may be used to treat brain tumours, or other small tumours that occur within the biological system.

The impedance matching proposed above allows the antenna to be optimised for measuring a range of tissue impedances representative of various anatomical structures and cancerous tumours (the information used here to model a cancerous tumour is based on the extrapolation of low frequency measurement data). Impedance measurements given in this specification are referenced to the proximal end of the surgical antenna structure.

The antenna may contain one or both of two impedance matching mechanisms or networks explained below. Preferably, the impedance matching arrangements are contained within the distal tip e.g. of a 7 French (2.2 mm outside diameter) structure. Preferably, the antenna structure is suitable for insertion percutaneously inside the human body, i.e. the physical structure may be rigid and the insertion tip may have a sharp point. To enable the structure to be used within the human body, the materials used are preferably biocompatible (or have biocompatible coatings) and preferably do not present any risks to the patient. For example, the separate insertion tip (distal tip cone) mentioned above is preferably securely attached to make sure it does not come off when inside the patient.

While the specific antenna embodiments described below are optimised for single frequency operation at 14.5 GHz, this invention is not limited to single frequency operation, for example, it may be desirable to operate the antenna over a frequency range of +/−50 MHz around the spot frequency of 14.5 GHz. The dimensions of the antenna can be selected or adjusted to accommodate any practicable frequency (or range of frequencies) where the underlying theory related to the current invention remains valid. This invention is not limited to using the same frequency for producing controlled ablation and tissue state measurements for example, the structure may be optimised to produce ablation at 5 GHz and tissue state measurements at 25 GHz. The antenna is preferably adapted for use with a frequency that enables the controlled ablation of small tumours (particularly suitable for the treatment of early stage breast cancers and other conditions where controlled ablation of small lesions is desirable), and also provides a depth of penetration of radiation in representative tissue structures that is small enough to enable localised dielectric measurements to be performed, i.e. the measurement information can be referenced to the distal tip of the antenna structure and the interference due to tissue structures adjacent or nearby the tissue structure of interest is minimised. This feature provides an advantage in terms of enabling the antenna to precisely locate the tumour to be ablated prior to initiating the ablation process.

The materials disclosed for use in the current invention may be used for similar surgical treatment and/or measurement antenna structures that are optimised to operate at other microwave frequencies. In this instance, the geometry of the structure can be adjusted in accordance with the particular frequency. Preferably electromagnetic field simulation tools are used to optimise the antenna structures. It is preferable for the diameter and/or the frequency to be such that modes other than the transverse electromagnetic mode (TEM) do not propagate inside the structure i.e. to prevent the structure from behaving like a cylindrical waveguide.

To facilitate accurate measurement of changes in phase and magnitude at the distal end of the treatment/measurement antenna, the complete antenna structure may exhibit a low insertion loss, and the variation of phase and magnitude as a function of changes in temperature of the structure itself, for example, due to dielectric or conductor heating, is minimised since large variations will place limitations on the measurement sensitivity capability of the system. Random phase and magnitude variations that occur within the antenna structure may make it difficult to determine the exact phase and magnitude variations that occur at the distal end of the antenna due variations of the tissue load. Any unquantifiable random variations that occur within the antenna structure may present a limitation on the measurement sensitivity of the system, hence it is desirable to give careful consideration to the materials used in the design of the antenna and it is preferable e.g. through the use of simulation to optimise the geometry of the antenna in order to provide optimal system measurement sensitivity capability.

Preferably, the antenna is operable in two treatment modes. The first mode is that of enabling microwave energy to be efficiently launched into a tumour to enable controlled ablation (or cell death) to be performed on cancerous tissue and to leave a controlled 'safe margin' of ablated healthy tissue around the site of the tumour. The second mode is to enable measurements of biological tissue characteristics to be performed. In this mode of operation the distal tip of the antenna preferably allows for small changes in complex impedance to be measured in order for the system to be capable of differentiating between various types of biological tissue (e.g. skin, fat, blood and tumour), to have the potential ability of being able to differentiate between various stages of cancerous growth, (e.g. benign and malignant states), and to be able to measure changes in tissue state that occur during the ablation process. The latter requirement relates directly to the first treatment mode; that of being able to efficiently launch energy into a tumour to enable controlled ablation (or cell death) to be performed on cancerous tissue and to leave a controlled 'safe margin' of ablated healthy tissue around the site of the tumour, since the measured information will govern the position of tuning stubs (or another tuning mechanism) used in a tuning filter used to dynamically impedance match an energy source to a tissue load (particular details of this aspect is given in WO 2004/047659). This information will also be used to calculate the energy required to ablate the tumour with the desired 'safe margin', and may be used to determine modulation requirements (pulse frequency and duty cycle), and average/peak power levels, thus it is extremely desirable for the antenna to be sensitive to small changes in dielectric properties (or impedance) seen at the distal end of the tip of the antenna.

The geometry, and choice of materials used in the antenna design, may be optimised using the Computer Simulation Technology (CST) electromagnetic field simulation tool, Microwave Studio®. Some results from the electromagnetic field optimisations are included below.

The present invention may also provide methods for producing a manufacturable solution for the ablation/measurement antenna that is capable of performing the functions described above. In this aspect, suitable manufacturing processes, choice of biocompatible materials and structures that can be directly inserted into the body to enable minimally invasive or percutaneous surgery to be performed are considered. In a preferred practical system, the following components are recommended: rigid stainless steel and copper (or silver) low loss composite structure with a low loss PTFE dielectric between the inner and outer conductor, a low loss ceramic (for example, alumina or zirconia) cone tip impedance transforming and matching structure for impedance matching the low loss PTFE with the dielectric constant of a representative tissue type load, a Parylene C coating for biocompatibility and for reducing the friction between the antenna and the tissue, and an additional tuning element to match out any unwanted inductive or capacitive element inherent within the antenna structure that may be present.

Since a microwave cable assembly and the antenna described here may form a single use disposable item, the complete assembly may be contained in a sterile package with only a small section of the cable assembly and the RF input connector, accessible to enable a connection to be made to the electronic instrumentation (generator).

BRIEF DESCRIPTION OF THE DRAWINGS

Examples of the present invention are described in detail below with reference to the accompanying drawings, in which:

FIGS. 1(a) and 1(b) show a surgical antenna which is a first embodiment of the present invention, FIG. 1(a) showing the complete antenna and FIG. 1(b) showing a cross-section of the tip;

FIGS. 17(a), 17(b) and 17(c) show a surgical antenna which is a seventh embodiment of the present invention, FIG. 17(a) showing the complete antenna and a cross-section of the tip, and FIGS. 17(b) and 17(c) showing a cross-section looking down the antenna axis.

DETAILED DESCRIPTION; FURTHER OPTIONS AND PREFERENCES

Figure 2A:
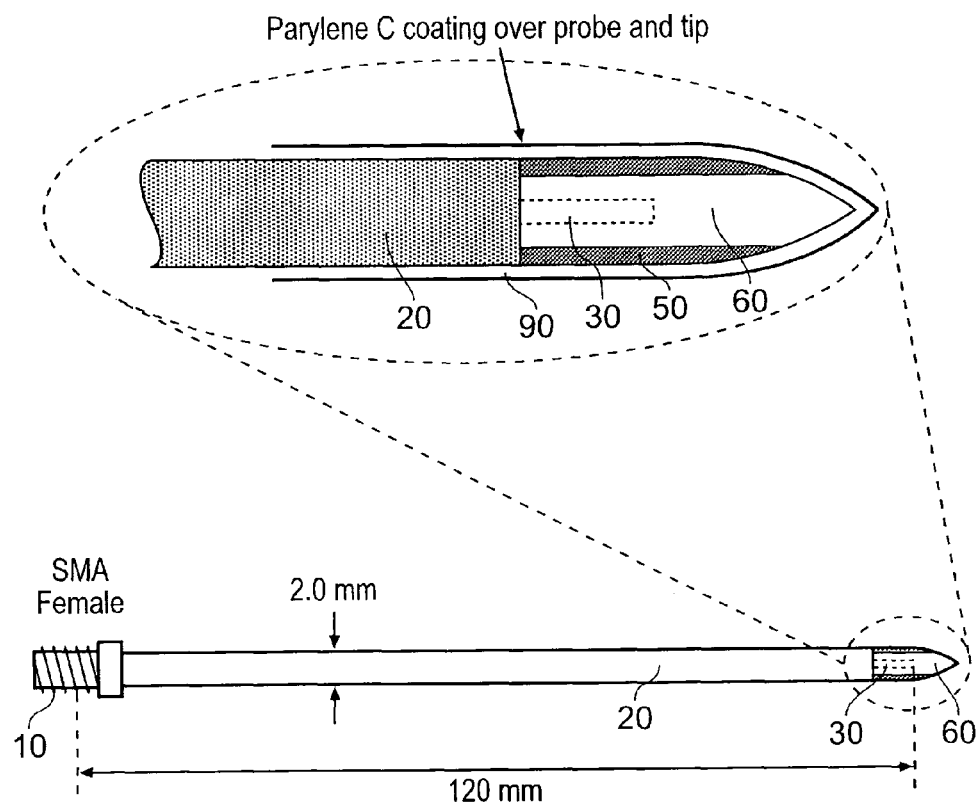
FIGS. 2(a), 2(b) and 2(c) show a surgical antenna which is a second embodiment of the present invention, FIG. 2(a) showing the complete antenna and a cross-section of the tip, and FIGS. 2(b) and 2(c) showing a cross-section looking down the antenna axis.

The description given below focuses on the design and development of the measurement/ablation antenna.

Details of materials used for practical implementation and means of manufacture are addressed. It is envisaged that the antenna will be a disposable item, hence design for manufacture will become an important feature of the antenna structure.

The impedance measurements given in this description for the optimised antenna structure are measured by attaching a measurement port to the proximal end of the antenna structure and the distal tip end fully immersed in a block of biological tissue that is described by a value of relative permittivity and conductivity (dielectric materials can be described by these two properties). Proximal end measurements are compared for various tissue types. Values of relative permittivity and conductivity for biological tissues used in the simulations presented here were obtained from the following reference: 'An internet resource for the calculation of the Dielectric Properties of Body Tissues in the frequency range 10 Hz-100 GHz', IFAC-CNR, Florence, Italy, 1997-2002, http://niremf.ifac.cnr.it/tissprop. In this work, the biological properties of the majority of the biological tissue types that constitute the anatomical structure have been measured over the frequency range of between 10 Hz and 100 GHz.

Ablation Aspect

The antenna used to treat breast tumours is an omni-directional aerial with a ceramic tip at the distal end that reduces to a point such that it is suitable for use in percutaneous or interstitial applications, whereby it is necessary for the structure to be inserted directly through the surface of the skin. The antenna may also be introduced through a secondary tube, for example the instrument channel of an endoscope or a bronchoscope. The shaft of the antenna is cylindrical in form and has a preferred outside diameter of 2.2 mm, although this invention is not limited to this specific diameter, for example it may be greater than 10 mm or less than 1 mm.

The shaft of the probe forms a co-axial transmission line that feeds microwave power to the radiating antenna. The antenna is preferably encased in a radome, and this casing is preferably conical in shape. It is also preferable for the maximum diameter of the cone, where it joins the metal shaft, to be equal to the diameter of the shaft. From the point of interface between the metal shaft and the ceramic cone, the structure will then reduce to a point. This point is preferably sharp to enable unaided piercing into skin or other biological tissue (human or animal).

It is desirable for the near field transmitted radiation pattern of the antenna when propagating into a tumour to be spherical. The antenna contained within the conical radome is to generate a spherical radiation pattern in the near field. The antenna is to operate with maximum emission efficiency when inserted into a tumour. The properties of the tumour, and other surrounding biological tissue have been taken into account in the design of the antenna to ensure that the radiation is focussed into the tumour. Electromagnetic field modelling may be performed to ensure that the efficiency of the antenna is optimised using the target tumour as the tissue load. The electrical properties of the material used for the cone determines the impedance match into the biological tissue and can be optimised to maximise the power transmission into certain tissue loads. The electromagnetic model includes the antenna in-situ within the biological tissue. The antenna is 'end-fed' from the co-axial shaft and is encased within a circular cone of a material with a first value of relative permittivity at the frequency of choice, and is surrounded by biological tissue with a second relative permittivity at the frequency of choice.

Factors that may be taken into account during the development of the antenna include: beam shape, transmission efficiency, co-axial feed arrangement, low loss dielectric materials, biocompatible materials, hard microwave materials, connectivity of components, dielectric properties of representative tissue loads, and ease of construction.

Design Considerations

The complex impedance of the co-axial structure used in this invention is nominally 50+j0 ohms (this is the typical characteristic impedance of a standard co-axial transmission line). The invention is not limited to using feed structures that have a characteristic impedance of 50+j0 ohms, for example, semi-rigid co-axial assemblies are commercially available that have impedances of as low as 10+j0 ohms and as high as 100+j0 ohms. The impedance represented by the biological tissue load may, for example, consist of a relatively low real part together with a capacitive reactance. In order to minimise energy reflection, it is necessary to place an impedance transformer between the co-axial structure (the transformer may be partially inserted inside the coaxial structure) and the tissue load to ensure that the maximum amount of energy is transferred into the load. The matching transformer may be a fixed structure which is optimised for a specific tissue load, a variable impedance matching filter (such as the triple stub tuner described in WO 2004/047659), or a combination of the two components. In the current invention, a fixed structure has been developed that can be used in combination with a triple stub arrangement described in WO 2004/047659, although the invention is not limited to being used with a triple stub tuner or any other tuning filter, and can be used as an independent invention where an antenna structure is required that is pre-matched to a typical load impedance, for example the impedance of a tumour. The advantage of using the antenna structure described here in combination with the triple stub tuning mechanism described in WO 2004/047659 is that it is possible to dynamically adjust the matching network to enable the antenna structure to launch energy into changing impedance loads, which, for example, may be a change in the impedance of the tumour as the temperature is increased or the ablation process is progressed. It may be desirable to impedance match into charred tissue in order to increase the zone of heating.

The simplest embodiment of an impedance transformer that could be used in the band of microwave frequencies described in this specification as those that could be potentially useful for tumour ablation and/or detection, is the quarter wave transformer. In this embodiment, a length of transmission line that is of a length equal to a quarter (or an odd multiple of a quarter) of the electrical wavelength at the frequency of interest, and of characteristic impedance equal to the square root of the product of the source and load impedances attached at either end, can be used to match said source impedance to said load impedance. The above is described mathematically by equation 1 given below:

$$Z_0 = \sqrt{Z_s \times Z_1} \qquad 1$$

where $Z_0$ is the characteristic impedance of the matching transformer (in ohms), $Z_s$ is the impedance of the source (in ohms), and $Z_1$ is the impedance of the load (in ohms). In this instance, $Z_s$ is the impedance of the co-axial structure, and $Z_1$ is the impedance of the biological tissue.

If, for example, a co-axial structure is used with an impedance of 50+j0 ohms, and the impedance of the biological tissue is 10−j20 ohms, then it would be necessary to insert a transformer with a characteristic impedance of 28.43+j17.57 ohms to produce the matched condition.

Figure 3:
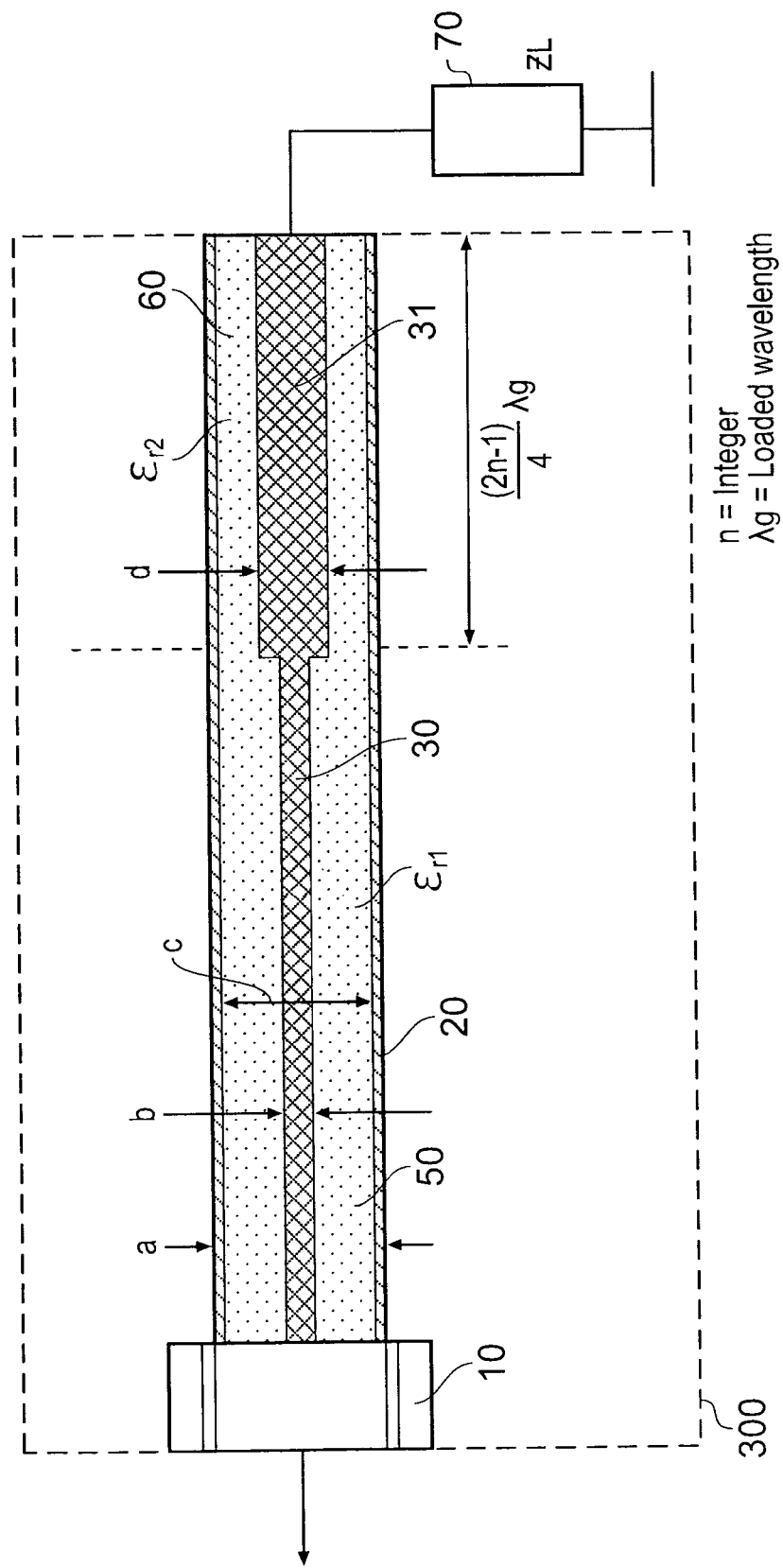
FIG. 3 illustrates an example of a quarter wavelength transformer that can be used in the antenna of the present invention.

A structure using a quarter wavelength transformer is shown in FIG. 3. It should be noted that it may be preferable to use a plurality of quarter wavelength transformers to form an impedance matching network. It may be desirable to adopt this design approach in the instance where the source impedance is significantly different to the load impedance, for example, where the source impedance is 10Ω and the load impedance is 1000Ω, and it is desired to efficiently couple the energy from the source into the load.

An alternative to using an impedance step transformer is to use pins or stubs inserted inside the co-axial structure. For example, two metal pins may be located near the distal tip of the antenna to produce a half wave filter. This arrangement may also serve the purpose of locating and holding the ceramic cone tip in place and alleviate the need for using glue (araldite or medically approved super glue) to secure the ceramic tip. The advantage of using a physical connection is that the arrangement is essentially temperature independent and there is no hazard of unwanted chemicals getting inside the body. The use of pins to achieve matching between the co-axial structure and the tumour will mean that the structure has a higher Q than would be the case if the design used a quarter wave impedance step transformer. It may also be preferable to use PTFE pins rather than metal pins. It should be noted that if araldite is used in the structure it should be de-gassed in a vacuum to prevent the formation of air bubbles.

It is normal for the dielectric material used in co-axial structures that are designed to operate in the microwave frequency region to be a low density PTFE material, for example expanded PTFE or PTFE tape, in order to minimise the insertion loss through the structure. The dielectric constant for such materials is low and is normally between 1 and 3. On the other hand, the dielectric constant for the tumour may be much higher, for example around 40, therefore, in order to be able to provide a good impedance match between the co-axial structure and the tumour to enable the energy from the source to be efficiently delivered into the tumour, i.e. to minimise the amount of power reflected back along the co-axial structure, it is necessary for the transformer to provide a means of matching the low dielectric PTFE with the high dielectric tumour; this may be achieved by using a third dielectric material with a value of dielectric constant between the value for PTFE and the tumour. It may also be preferable to use a material with a dielectric constant that gradually changes along the length of the transformer in order to provide a non-abrupt change from the low dielectric constant to the high dielectric constant representative of the co-axial structure and the tumour respectively. For example, it may be preferable to sandwich a plurality of materials together, each of length equal to an odd multiple of a quarter of the electrical wavelength to form the transformer.

It was found from previous work that a simple monopole antenna construction resulted in the power absorption being concentrated around the end of the outer sheath of the co-axial structure; this condition may result in there being insufficient heating at the tip of the inner conductor to cause the cancerous cells to be destroyed. It is also preferable for the radiation to be delivered in the forward direction from the end of the antenna in order to control the volume of ablation of target treatment tissue and to create a spherical volume of ablated tissue. The breast tumours that will be treated using the antenna described here will normally be spherical in shape.

FIG. 1 shows the structure of the antenna that has been developed to address the requirements given above for controllably treating breast tumours and for differentiating between normal tissue and cancerous tissue. FIG. 1(a) shows the overall antenna structure, consisting of a microwave connector 10 connected to the proximal end of the antenna. This connector may be an SMA, N-type, or MCX, for example, and may be male or female in gender; the antenna developed for this work used an SMA female connector. It may be preferable not to use a connector at the proximal end of the antenna, but to integrate the antenna with a suitable energy delivery cable assembly (not shown). Connector 10 is attached to a rigid co-axial cable 20, which is preferably stainless steel, and the distal end of the co-axial cable 20 is attached to the radiating antenna section of the structure (the aerial). The antenna and a portion of co-axial cable 20 are shown immersed inside a volume of tissue 70; this, tissue may be a tumour.

FIG. 1(b) shows details of the radiating section of the antenna that has been developed to enable controlled ablation of spherical tumours and to allow for impedance information to be measured at the proximal end of the structure 10 to provide information regarding the type of biological tissue (or the state of the tissue) that is in contact with the distal tip of the antenna (the aerial). The aerial comprises of a co-axial feed structure consisting of an outer conductor 20, an inner (or centre) conductor 30 and a first dielectric 50. A second dielectric 60 is shown inserted inside the co-axial structure, with the centre conductor 30 extending through (or into) the centre of second dielectric material 60. Said second dielectric 60 forms an impedance transformer to enable the first dielectric 50 to be matched into a third dielectric that is represented by the volume of tissue (or tumour) 70. A second matching element 40 is also included; this element is a metal ring (or swage) and is used to enhance the impedance match into a representative 'dummy' model for a tumour 70. The second dielectric 60 is a hard material and is shaped in the form of a cone with a pointed tip to allow percutaneous insertion through biological tissue 70. The outer conductor (or jacket) 20 is preferably a bimetallic construction, which uses stainless steel to form the outer section to enable the structure to be biocompatible and rigid to provide the necessary strength to enable the structure to be directly inserted through the various tissue types until the tumour is located, and uses a material with a higher conductivity, for example, copper or silver, to form the inner section to enable the microwave signal to propagate with low loss. Due to the use of high microwave frequencies (circa 14.5 GHz), the microwave energy will be concentrated in less than 10 μm of wall thickness due to the fact that the skin depth at 14.5 GHz is around 1 μm for the materials that would be considered for use in the design and that 99.9% of the energy flows in five skin depths of material. This feature enables the majority of the outer conductor to be constructed using stainless steel to provide the required rigidity and a higher conductivity material to be used as the inner layer of the outer conductor. The results from theoretical calculations of thickness of metallisation for silver, copper and steel at 14.5 GHz are given in table 1. This gives values for required thickness of metallisation for 90%, 99% and 99.9% of power flow.

TABLE 1

Thickness of metallization requirements for second section of outer conductor 20

| Power transferred (%) | Silver | Copper | Steel |
|---|---|---|---|
| | Thickness of metallization (μm) | | |
| 90 | 1.23 | 1.26 | 4.30 |
| 99 | 2.46 | 2.53 | 8.61 |
| 99.9 | 3.68 | 3.79 | 12.91 |

It is also preferable for centre conductor 30 and swage 40 to be made from materials that exhibit high conductivity in order to minimise conductor loss, reduce the overall insertion loss of the structure and to minimise structural heating. First and second dielectric materials 50 and 60 respectively should also exhibit a low dielectric loss at the frequency of interest to help reduce the overall insertion loss of the structure and to minimise structural heating. The dielectric loss can be quantified by the quality factor (Q) or the loss tangent (tan δ), which provide a measure of the amount of power dissipated or lost in the material. Formal definition: Q=power (energy) stored/power (energy) dissipated (or lost) and tan δ=1/Q.

Figure 2B:
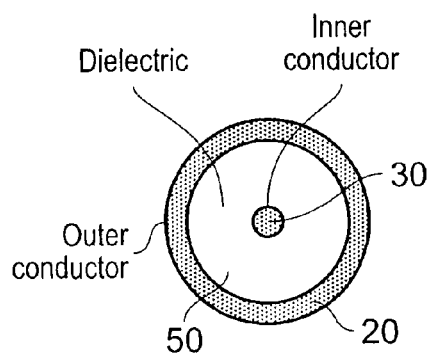
Figure 2C:
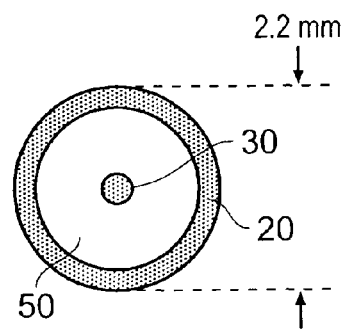

For the practical construction of the antenna, a portion of first dielectric material 50 has to be removed (or cut-back) from inside the co-axial assembly and the second dielectric 60 may have a curved profile. Small air gaps may exist between the second dielectric 60, and the following interfaces: the inner surface of outer conductor 20, the outer surface of inner conductor 30, the metal ring (or swage) 40, and the first dielectric 50. Since these air gaps will exist in practice, they have been taken into account in the electromagnetic field modelling performed on the antenna structure. The cut-away in the first dielectric 50 was up to 7 mm, and since the preferred material for 50 is PTFE, it has to be ensured that the soft PTFE 50 is not squashed by the hard material 60 or that an excessive air gap exists between the two materials. The preferred material for the second dielectric 60 is a low loss ceramic material, for example alumina (more details of specific materials that can be used will be considered later in this description). It may be preferable to add a conformal coating of biocompatible material to the outer surface of second dielectric material 60 and a portion of outer conductor 20. A suitable material is Parylene C, and a coating thickness of around 10 μm may be applied without affecting the aerial design in terms of the structure being capable of delivering controlled energy for ablating spherical tumours and having the measurement sensitivity required to enable various tissue types and tissue states to be identified. The coating of Parylene C may also be used to ensure that moisture or ingress cannot get into the structure at the interface between the co-axial cable (more specifically, the outer conductor 20) and the second dielectric material 60. The coating of Parylene C will also help to reduce the coefficient of friction on the surface of the antenna. In the construction of the antenna it may be preferable to pre-heat the PTFE to allow for expansion, i.e. once the PTFE has been heated and expands, it should remain stable when subsequently used. It may also be preferable to remove the 7 mm of PTFE by freezing the PTFE to remove it, cut it back by 7 mm using a sharp scalpel blade and then re-inserting it whilst still frozen FIG. 2(a) shows an antenna structure similar to that described above with a coating of biocompatible material 90 applied to the outer surface of the structure. FIGS. 2(b) and 2(c) show cross-sections of the co-axial structure.

FIG. 3 shows an arrangement where the impedance transformer is an integral part of the co-axial structure. In this arrangement the impedance transformer comprises of a co-axial section with an electrical length of an odd multiple of a quarter of the loaded wavelength at the frequency of interest and of an impedance that is equal to the square root of the product of the tissue load impedance ($Z_L$) 70 and the source impedance ($Z_s$). If there are no other transformations present in the structure and the characteristic impedance ($Z_o$) of the first section of the co-axial feed cable is 50Ω, then it may be assumed that the source impedance ($Z_s$) is also 50Ω, thus the following formula describes the impedance of the first section of the antenna structure:

$$\frac{138}{\sqrt{\varepsilon_{r1}}} \log_{10} \frac{c}{b} = 50\Omega, \qquad 2$$

where $\in_{r1}$ is the relative permittivity of first dielectric material 50 (dimensionless), c is the inner diameter of the outer conductor 20 (in metres), and b is the outer diameter of the first inner conductor 30 (in metres).

Equation 3 describes the impedance of the second section, which is used to match the impedance of the first section with the impedance of the tissue load 70:

$$\sqrt{Z_l} \times \frac{138}{\sqrt{\varepsilon_{r2}}} \log_{10} \frac{c}{d} = \frac{138}{\sqrt{\varepsilon_{r1}}} \log_{10} \frac{c}{b}, \qquad 3$$

where $\in_{r2}$ is the relative permittivity of second dielectric material 60 (dimensionless), and d is the outer diameter of the second inner conductor 31 (in metres).

The length of the second section (the impedance transformer) is formally described using equation 4

$$L = \frac{(2n-1)v}{4f\sqrt{\varepsilon_{r2}}}, \qquad 4$$

where L is the physical length of the transformer (in metres), n is any integer value (dimensionless), v is the speed of light in vacuum or air (3×10⁸ m/s), and f is the frequency of operation (in Hz).

In a similar manner, the values of dielectric constants for the first section $\in_{r1}$ 50, the second section $\in_{r2}$ 60 and the tissue load $\in_{r3}$ 70 can be used to impedance match the structure. The relationship that exists between the three dielectric constants is formally described using equation 5

$$\sqrt{\in_{r1} \times \in_{r3}} = \in_{r2}. \qquad 5$$

The loss tangent (tan δ) for $\in_{r1}$ and $\in_{r2}$ should be as low as possible to prevent energy from being dissipated in the antenna structure, causing the structure to heat up and to minimise power loss through the structure (or insertion loss).

The properties of the biological tissues that are used for the electromagnetic modelling are relative permittivity ($\in_r$) and conductivity (σ), which vary as a function of frequency. The following reference was used to obtain values of $\in_r$ and σ for the various biological tissue types used for this work: 'An Internet resource for the calculation of the Dielectric Properties of Body Tissues in the frequency range 10 Hz-100 GHz', IFAC-CNR, Florence, Italy, 1997-2002, discussed above. If it is assumed that a transverse electromagnetic (TEM) wave propagates in the tissue, then equation 6 can be used to calculate the complex impedance from values of $\in_r$ and σ obtained from the above-mentioned reference resource. This provides a first order approximation that can be used for modelling purposes and for calculating the value of characteristic impedance required for designing the matching transformers used in this work.

$$Z = \sqrt{\frac{j\omega\mu_0\mu_r}{\sigma + (j\omega\varepsilon_0\varepsilon_r)}}, \qquad 6$$

where Z is the complex impedance of the tissue (ohms Q), j is the complex impedance operator=$\sqrt{-1}$ (dimensionless), ω is the radian frequency=2πf Hz, $\mu_0$ is the permeability of free space=4π×10⁻⁷ H/m, $\mu_r$ is the relative permeability (dimensionless), $\in_0$ is the permittivity of free space=8.854×10⁻¹² F/m, and $\in_r$ is the relative permittivity (dimensionless) and σ is the conductivity (Siemens per metre or 1/ohms metres).

The electromagnetic field modelling package Computer Simulation Technology (CST) Microwave Studio® was used to model the antenna structures described in this specification.

Figure 4:
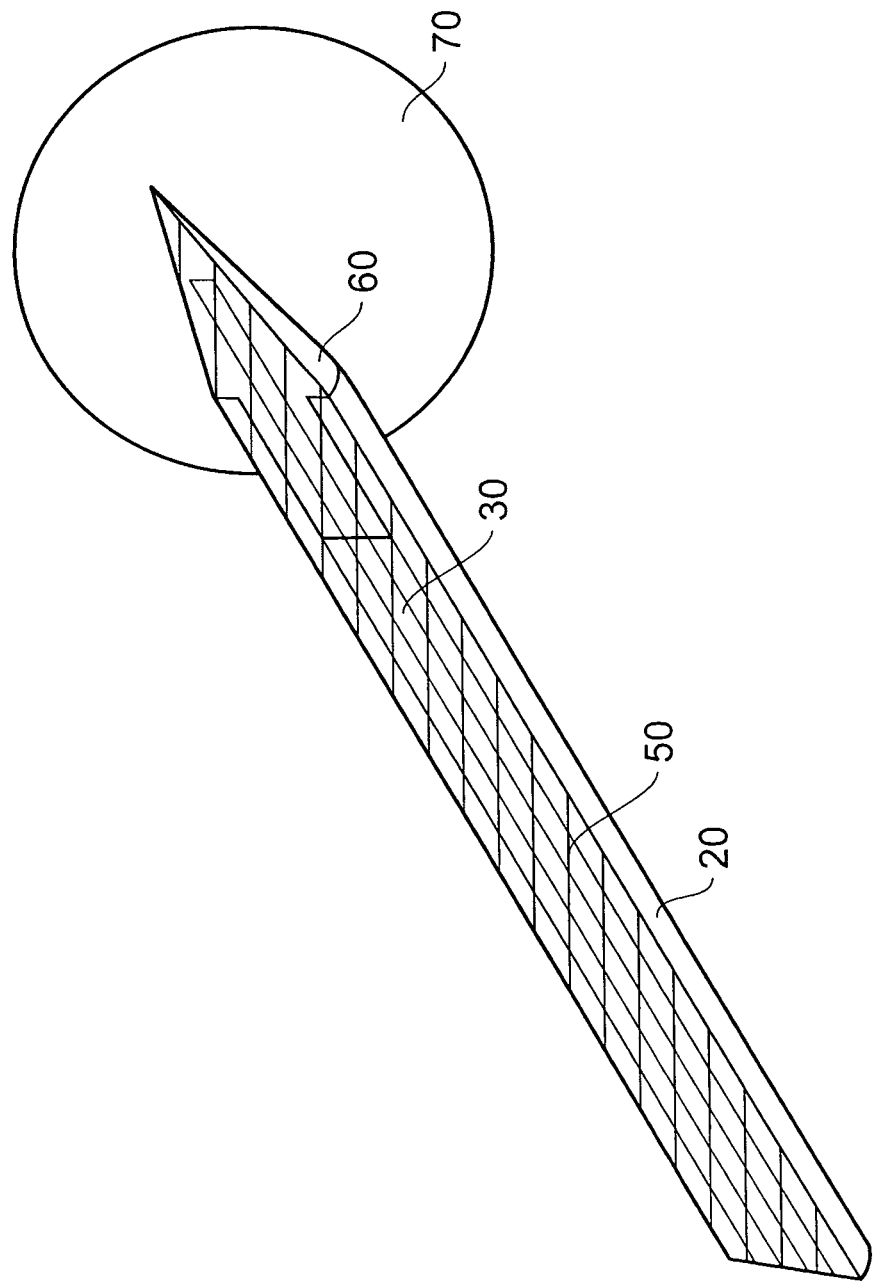
FIG. 4 shows a cut away perspective view of a surgical antenna which is a third embodiment of the present invention.

FIG. 4 shows the structure of the antenna that was used for the electromagnetic field simulations. The model shows the structure that has been cut along the 'Z' axis in a plane parallel to the 'Y' axis. In this model, the inner and outer conductors, 30 and 20 respectively, are specified as being made from copper with a conductivity of 5.8×10⁷ Siemens per metre (S/m), the first dielectric material 50 is PTFE with a relative permittivity of 2.08 and a loss tangent (tan δ) of 0.0001 at frequencies that lie within the microwave band that is of interest in this work, and the second dielectric material 60 is alumina with a relative permittivity of 9.9 and a tan δ of 0.0004. The relative permeability for all materials used has been assumed to be unity; this is a valid assumption since there should be no magnetic components in any of the structures used in this work. The inner conductor 30 has an outer radius of 0.254 mm, and the outer conductor 20 has an outer radius of 1.08 mm and an inner radius of 0.762 mm. The first dielectric material 50 has an outer radius of 0.762 mm and an inner radius of 0.254 mm. The alumina tip is pointed to enable the structure to be sharp to allow for unaided percutaneous insertion into tissue.

For the electromagnetic field modelling undertaken in this work, the Smith chart and energy profiles around the antenna structure are used to show the effectiveness of the designed antenna structure in terms of its ability to launch energy into various representative tissue loads. The models used in this work for evaluating the energy profiles produced by the antenna structure are: air, fat and tumour.

Figure 5:
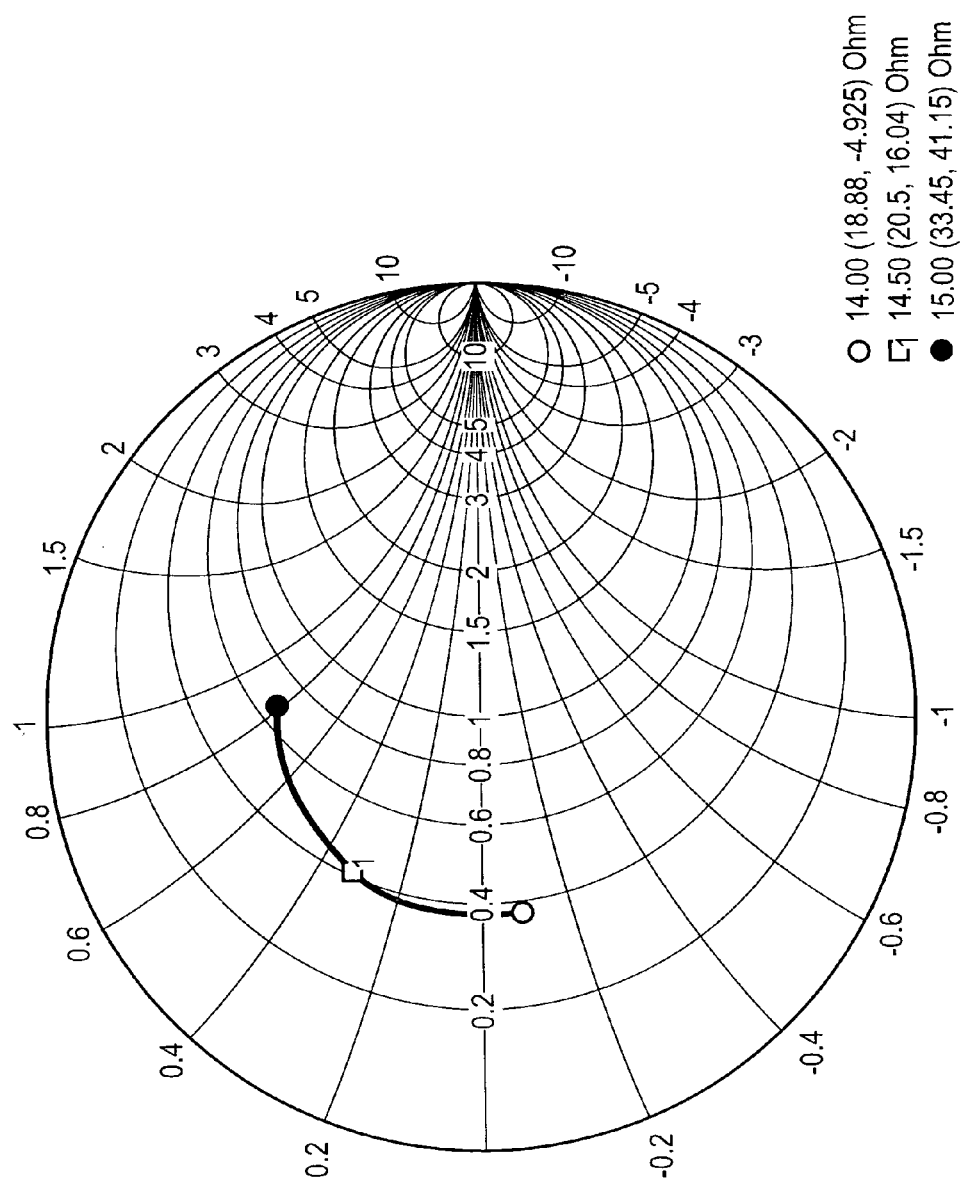
FIG. 5 is a Smith chart showing the impedance matching of the antenna of FIG. 4 into air.

The Smith chart provides a means of indicating the impedance match between the antenna and the tissue load. More specifically, the impedance match between the distal tip of the antenna (the aerial) and a volume of tissue. The Smith Chart enables any impedance to be plotted. The Smith chart is based on two sets of orthogonal circles used to express impedance (Z) as a combination of two components: Z=R+/−jX, where R is the resistive, or real, component, and X is the reactive, or imaginary, component. Both real and imaginary components must be used to characterise the impedance, for example, a 500 system is formally described as: 50+j0 Ohms. The Smith charts used in this work are normalised to 50Ω, thus the centre of the chart is 1.0 and all the impedances shown are divided by this characteristic impedance of 50Ω. Referring to FIG. 5, the resistive (real) part of the impedance (R) can be found along one of the complete circles shown, where the values shown are given by: R/50, and the reactive (imaginary) part (X) can be found along one of the lines that show up as arcs, where the values shown are given by: jX/50. Two additional features on the illustrated Smith chart are (1) a horizontal line of numbers representing pure resistance and a circle of numbers on the outside circumference representing pure reactance, an upper region above the horizontal line (but not around the circumference) therefore representing a combination of resistance and inductive reactance, and a lower region below the horizontal line (but not around the circumference) representing a combination of resistance and capacitive reactance, and (2) the fact that the closer the position of the marker (or point of interest) to the 1.0 position on the horizontal line, the better the impedance match between the 50Ω system and the load (biological tissue or air). For example, if the marker is exactly on the horizontal line at the 1.0 position then the 50Ω system is perfectly matched into the load and no reflection of energy will occur. Put in another way, in this instance, the generator is matched with the load and there will be no power reflected back along the co-axial feed cable hence there will be no standing waves set up along the co-axial cable between the generator and the load.

In the models presented in this work, the load at the distal tip of the antenna is represented by a cylinder of 40 mm in length by 20 mm in diameter. This volume was chosen because it is large enough to absorb all the energy launched into the biological materials of interest when operating at a frequency of 14.5 GHz since these materials are lossy and, therefore, will absorb all of the energy over a short distance. Also, the propagation of the energy is infinite in air so long as matched boundaries are used. The limited volume used here also enables the simulations to take around 15 minutes to run, but if the diameter was to be increased from 20 mm to 40 mm then it could take up to 3 hours for each simulation to run; thus it would not be practicable to run the simulator several times in order to perform an optimisation process.

FIG. 5 shows three points on Smith Chart that indicate the match between the 50Ω system and air. The complex impedance of interest is that at 14.5 GHz, where the value is: 20.50+j16.04Ω, which gives a return loss of 6.66 dB since return loss is the ratio of power delivered to power reflected in order to maximise the power delivery into the tissue, it is desirable for the return loss to be as high as possible for example a 10 dB return loss indicates that approximately 90% of the energy will be delivered into the tissue load. It can be seen from FIG. 5 that the marker at 14.5 GHz is away from the 1.0 position, thus it is expected that there will not be a good impedance match between the load and the 50Ω system. This implies that a large amount of the power will be reflected back along the antenna; which is desirable in this instance. It is desirable for the antenna not to propagate energy into free space, thus it is preferable for there to be a mismatch between the distal tip of the antenna and air. It is preferable for the antenna structure to be used with the instrumentation described in WO 2004/047659 and WO 2005/115235, where a free space load will be sensed and the power level will be backed off to a safe value to avoid propagation into free space.

Figure 6:
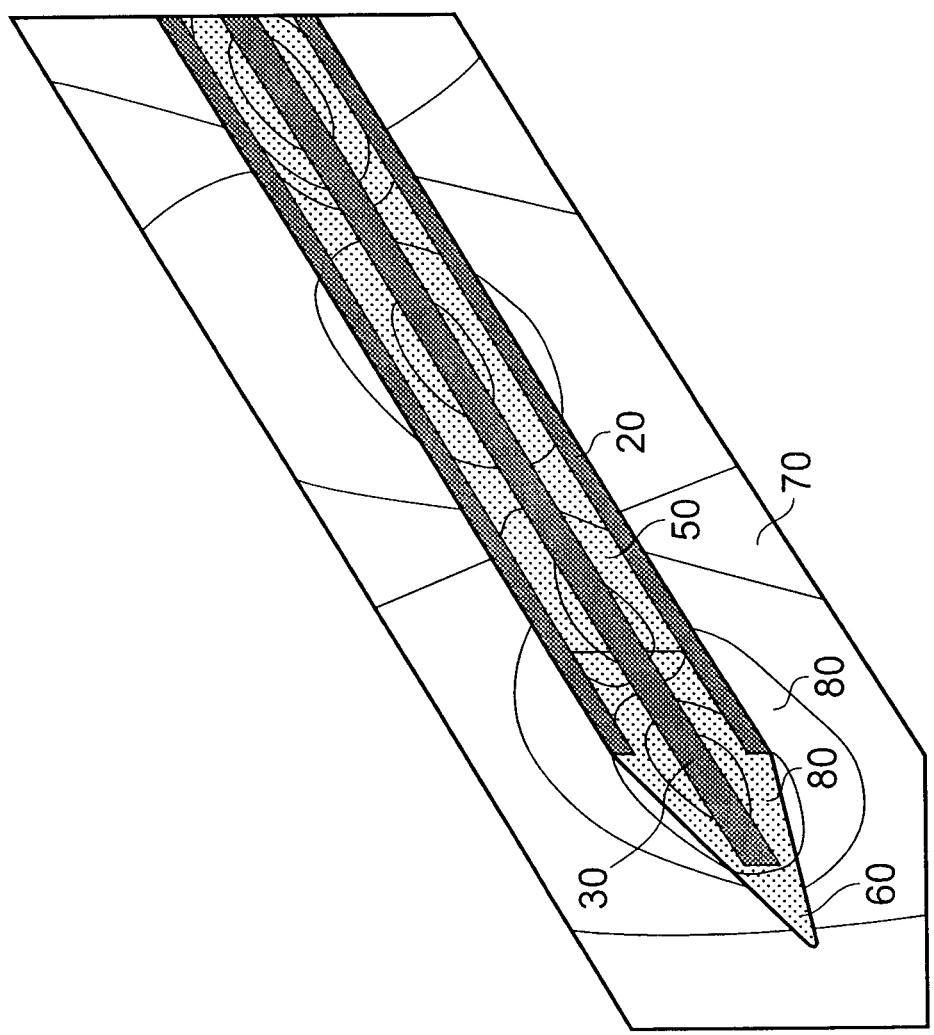
FIG. 6 is a diagram showing a simulated distribution of current density inside and outside the antenna of FIG. 4 when in air.

FIG. 6 shows a simulation of current density inside and outside the antenna structure with air 70 as the load. The contours of current density 80 indicate that it is maximal around the centre conductor and the level returning along the outside of the structure is much less, hence sheath currents are minimised. This is a desirable feature of the design since excessive sheath currents will cause heating along the outer shaft and make energy delivery from the tip less efficient.

Figure 7:
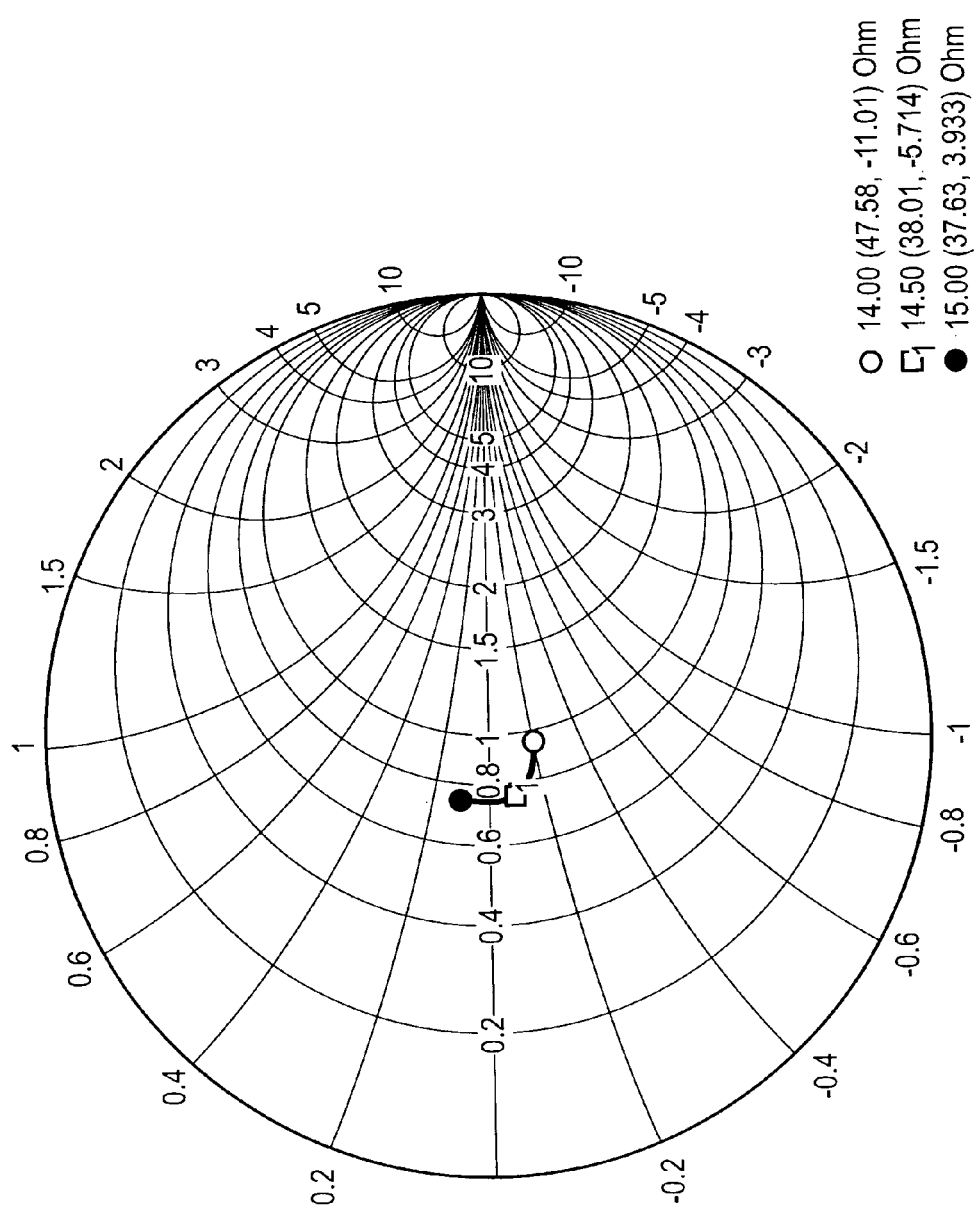
FIG. 7 is a Smith chart showing the impedance matching of the antenna of FIG. 4 into fat tissue.

FIG. 7 shows three points on Smith Chart that indicate the match between the 50Ω system and fatty tissue 70. The complex impedance of interest is that at 14.5 GHz, where the value is: 38.01Ω−j5.714Ω, which gives a return loss of 16.66 dB. This implies that there is a good impedance match between the distal tip of the antenna (the aerial) and the tissue load 70.

Figure 8:
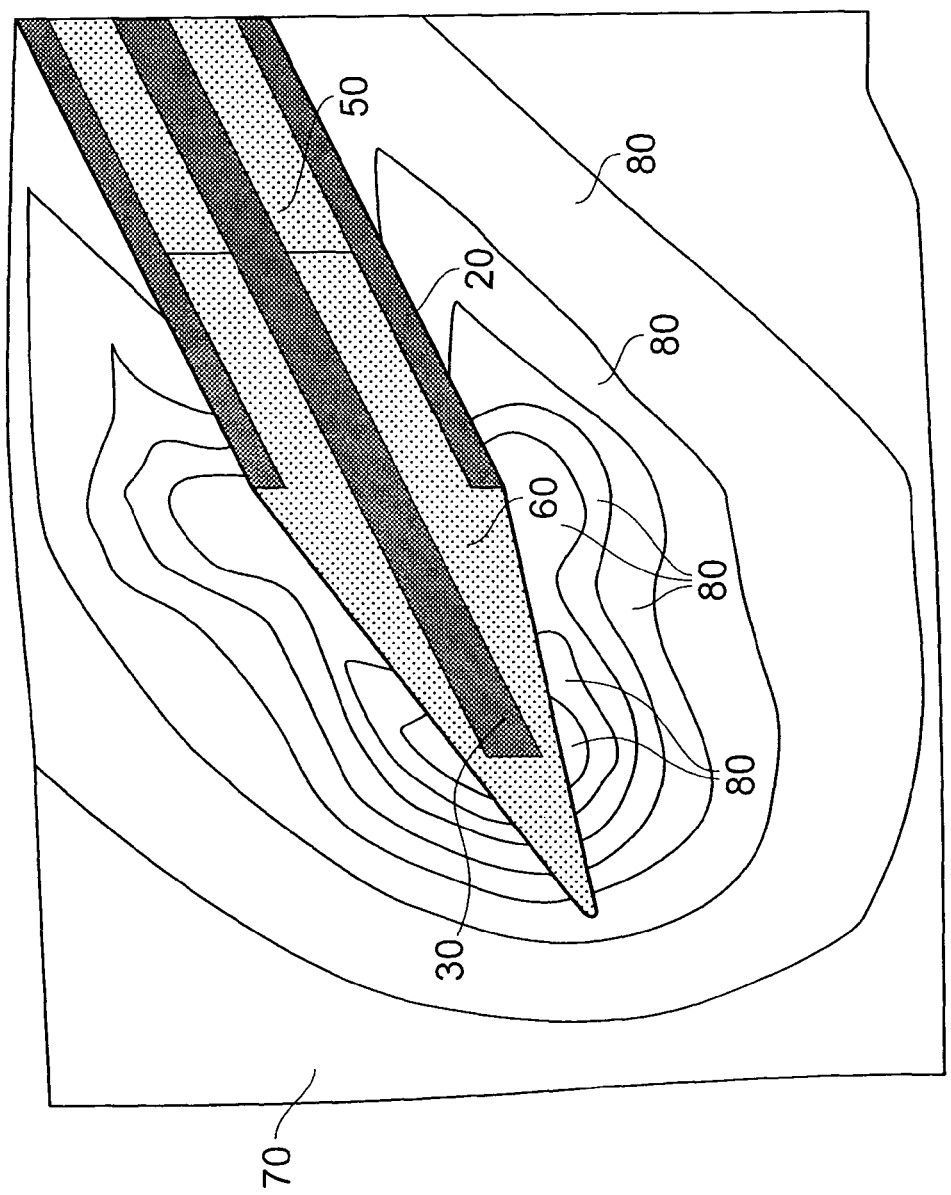
FIG. 8 is a current density distribution chart showing the current density inside and outside the antenna of FIG. 4 when in fat tissue.

FIG. 8 shows the power density (or energy absorption) 80 into fatty tissue 70. It can be seen that the power is distributed around the region of the tip and, unlike the case for the standard monopole antenna without the ceramic matching transformer, the power is delivered out of the end of the antenna, which is desirable. In the case of the standard monopole, it was found that the power absorption was concentrated around the end of the outer conductor 20 of the antenna structure, thus there may not have been sufficient heating at the tip of the inner conductor 30 to destroy cancerous tissue.

Figure 9:
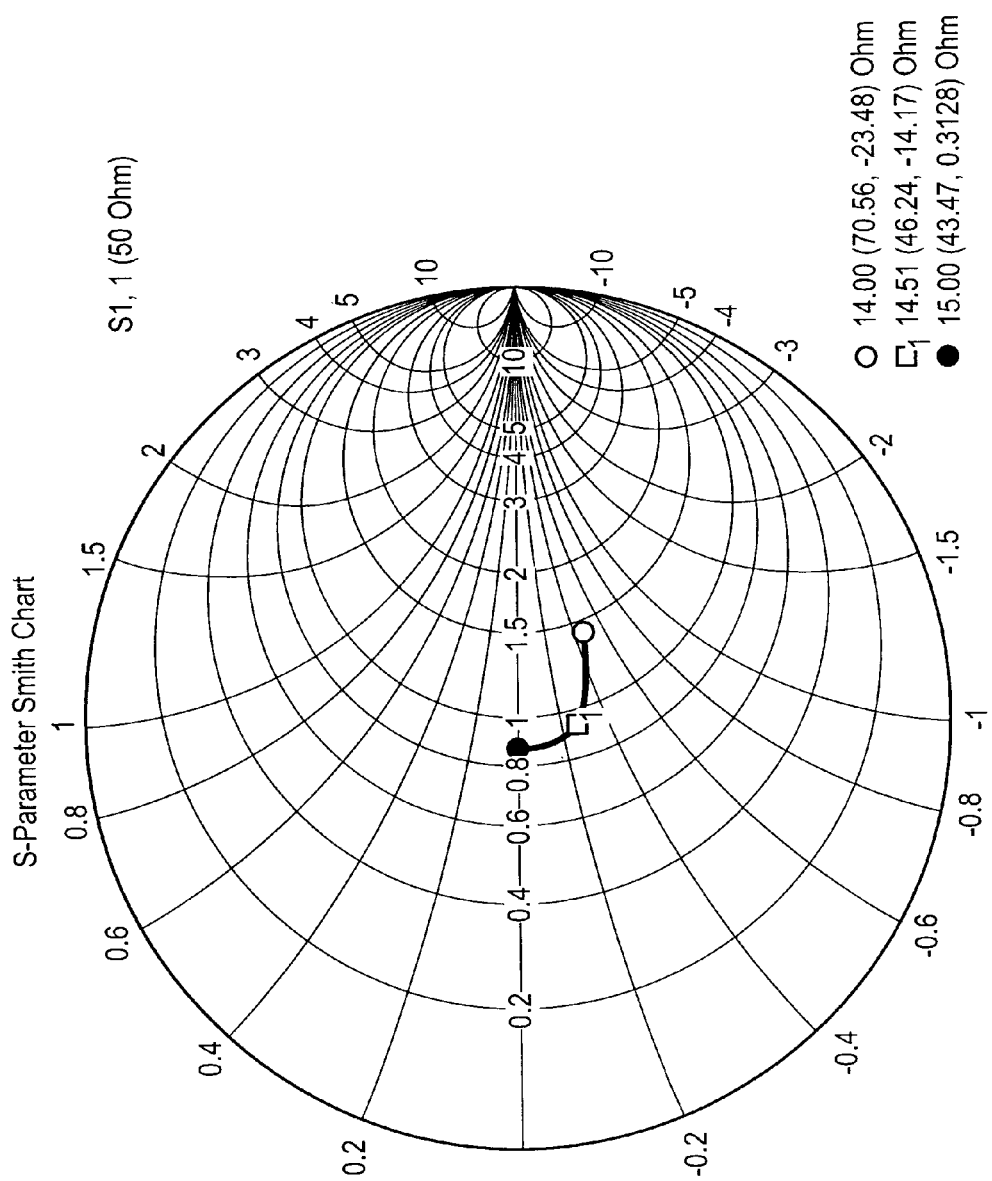
FIG. 9 is a Smith chart showing the impedance matching of the antenna of FIG. 4 into tumour.
Figure 10:
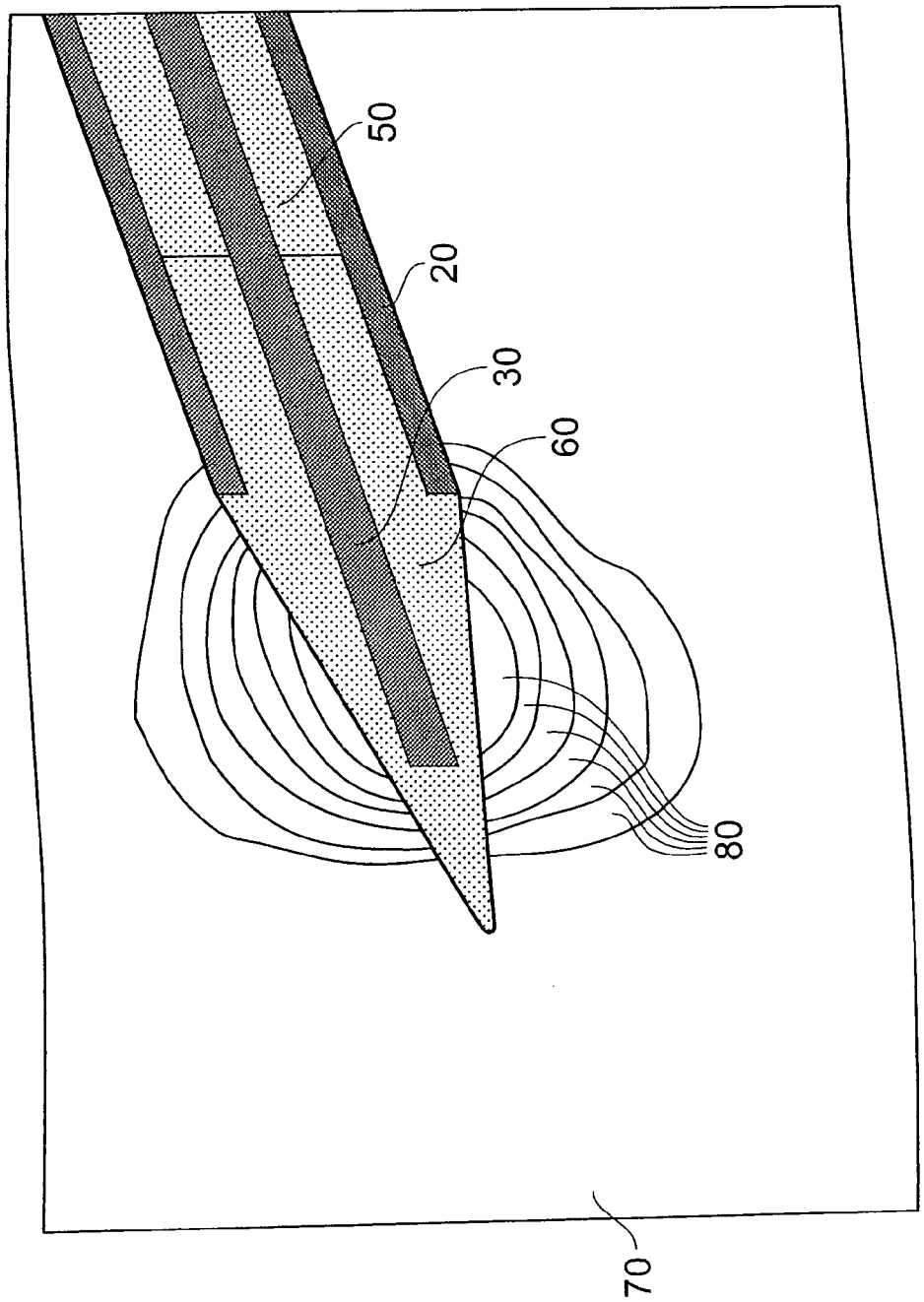
FIG. 10 is a current density distribution chart showing the current density inside and outside the antenna of FIG. 4 when in tumour.

FIG. 9 shows three points on Smith Chart that indicate the match between the 50Ω system and the tumour model 70. The complex impedance of interest is that at 14.5 GHz, where the value is: 46.24Ω−j14.17Ω, which gives a return loss of 16.66 dB. This implies that there is a good impedance match between the distal tip of the antenna (the aerial) and the tissue load 70. FIG. 10 shows the power density (or energy absorption) 80 into the tumour model 70. It can be seen that the power is distributed around the region of the tip and that the energy profile 80 is spherical. The energy distribution also indicates that no energy flows back along the shaft of the antenna and that the structure should enable controlled ablation to be performed. It was found during the design of the preferred structure that the inclusion of a controlled swage (see FIG. 1, item 40), which may be a slow rolling of the edge around the co-axial body with a slowly controlled and measured increase in depth so that minimal pressure is applied to the ceramic, enabled a better impedance match into the tumour model 70.

The shape of the ceramic matching transformer 60 has been optimised to give a good impedance match into the 'dummy' tumour model 70, which uses a value of dielectric constant of 40 and a loss tangent of 0.5 at a frequency of 14.5 GHz (this indicates that the tumour is a very lossy material). It is possible to adjust the geometry to match other tissue types or to use a different model for the tumour 70. In the final design, the conical tip 60 has the effect of diffracting the radiation from the antenna slightly in the forward direction (see FIGS. 8 and 10). The power absorption 80 in fatty tissue or tumour 70 is the greatest near the tip of the inner conductor 30. In tissue, the heating near the end of the outer conductor 20 is less than at the tip of the inner conductor 30 and the power flowing back down the outside of the co-axial structure is minimal, hence sheath currents are minimised. These results indicate that it should not be necessary to use an additional choke or balun in the antenna structure to prevent sheath currents flowing down the outside of the co-axial structure that may cause collateral damage or ablation at undesirable sites. This results in a less complicated structure, which should be easier to manufacture. The simulation results show that most of the energy delivered by the antenna is absorbed within a few diameters of the co-axial cable structure, i.e. around 6 mm. This is because the high dielectric constant and large loss tangent result in a large imaginary refractive index, which is proportional to the attenuation in dB per wavelength. Heating to a larger radius will be by thermal conduction from the heated tissue, unless the electrical properties of the already heated tissue change so that there is less attenuation through it.

Good impedance match into tissue of interest means that the voltage standing wave ratio (VSWR) should be low and large standing waves should not occur when high power levels, for example, 50 W or 100 W, are delivered into tumour or fatty tissue, before charring takes place. If the VSWR remains low after charring, the power and voltage handling requirements for the components used in the antenna structure, for example the microwave connector 10 connected to the proximal end of the antenna structure, will be limited.

Materials and Manufacture

Figure 11A:
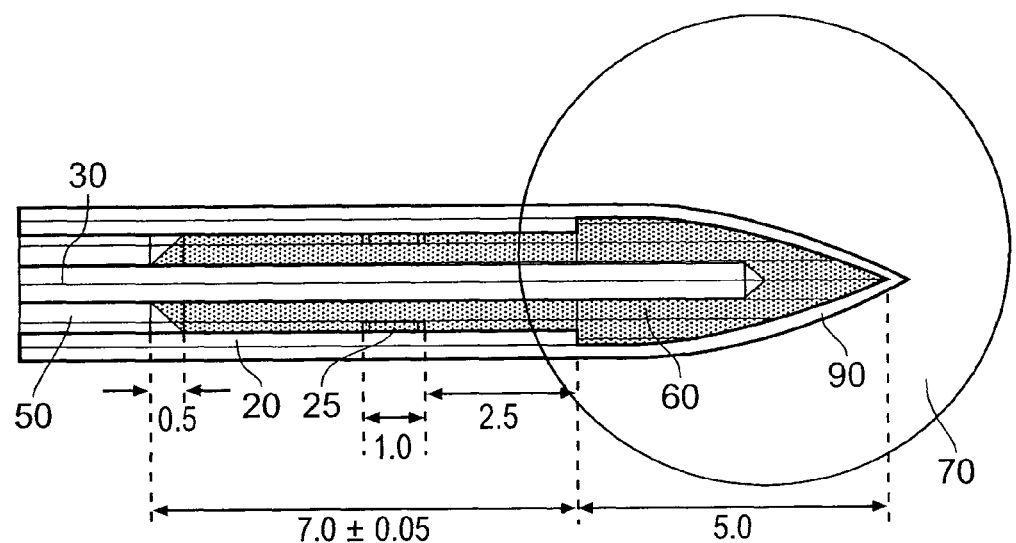
FIGS. 11(a) and 11(b) show a cross-section of the tip of a surgical antenna which is a fourth embodiment of the present invention, FIG. 11(a) showing the complete tip and FIG. 11(b) showing a magnified cross-section of its distal end.
Figure 11B:
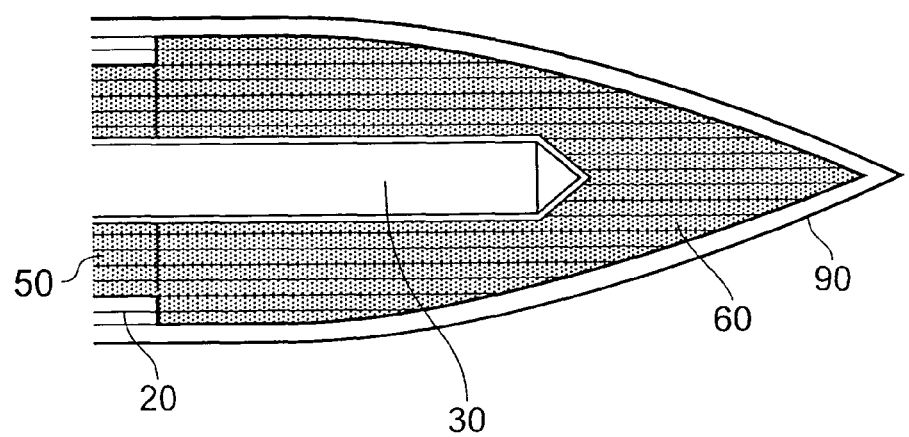
Figure 11C:
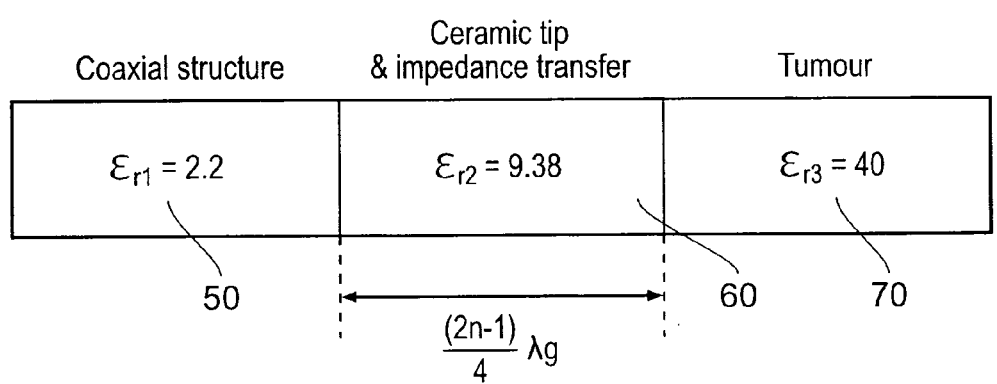
FIG. 11(c) shows a schematic representation of the impedance matching of materials that can be applied in the antenna of the present invention.

FIGS. 11(*a*) and 11(*b*) show a specific embodiment for the breast cancer treatment/measurement antenna described in this specification. This arrangement uses a rigid co-axial structure where the outer conductor 20 is a bimetallic construction of stainless steel and copper, and the inner conductor 30 is a bimetallic construction of silver plated solid copper-clad steel. The outer diameter of the outer conductor 20 is 2.20 mm+/−0.02 mm, and the outer diameter of inner conductor 30 is 0.51 mm+/−0.01 mm. The dielectric between the inner and outer conductors, 30 and 20 respectively, 50 is solid PTFE, with an outer diameter of 1.67 mm+/−0.02 mm. An advantage of using solid PTFE rather than tape wrapped PTFE is that it may be possible to use a custom made tool to remove the required 7 mm of material from the inside of the tube to enable the ceramic transformer 60 to be inserted in to the structure. The thickness of the copper that forms a part of 20, and is immediately adjacent to the dielectric material 50 is 76.2 μm and this layer acts as the primary conductor at the frequency used here of 14.5 GHz. Other parameters of the co-axial structure used include: impedance=50Ω+/−10, capacitance=96.1 pF/m, inner conductor DC resistance=21Ω/100 m, dielectric strength=5 kV RMS, higher order mode cut-off frequency=60 GHz, and maximum operating temperature=200° C. An SMA female connector 10 was soldered to the proximal end of the co-axial structure. The distal end was prepared to enable the co-axial structure to accept the ceramic tip transformer 60 by cutting-back 7 mm+/−0.05 mm of the PTFE dielectric 50 from the distal end of outer conductor 20, and leaving a length of 3.05 mm+/−0.02 mm (including a 0.3 mm taper) of inner conductor 30 protruding from the end of the outer conductor 20. The co-axial cable assemblies used in the development of the antenna described in this work were obtained from elspec GmbH (Brunnenfeldweg 5a, D-82538 Geretsried, Germany http://www.elspec.de).

A ring or swage was made from silver (other low conductivity materials e.g. copper, brass, gold or aluminium may also be used) and inserted into a 1 mm groove 25 made in the ceramic transformer 60. The purpose of this ring was to provide an optimal impedance match into the tumour model 70. It was found that the ring improves the match to most tissues. The ring may be slightly oversized to allow for the ceramic cone 60 to be fitted with an interference fit inside the co-axial structure to prevent the ceramic cone from pulling out of the antenna structure whilst inserted inside tissue. It is preferable for the ring to be fitted to the ceramic cone 60 before the cone is inserted inside the co-axial structure. If the ring can be used to hold the ceramic cone in place, it alleviates the need to use adhesive inside the structure. If the pressure exerted on the ceramic by the ring is fairly even then the ceramic will not break since ceramic is strong in compression. It may be necessary to hold the ceramic cone 60 inside the co-axial structure using a medically approved araldite or super glue. Examples of super glues that may be used are: 4011 surface insensitive instant adhesive or 3341 visible light curing adhesive, both from Henkel Loctite. These products are ISO 10993 certified or USP Class VI approved, are safe and non-toxic, and are fast curing at room temperature. More preferably, the ring can be soldered to the outer conductor of the co-axial structure to secure the ceramic tip in position. For example, before inserting the tip into the co-axial structure, one or two turns of 0.1 mm or 0.2 mm silver wire may be wound inside the groove in the ceramic tip and then a small amount of solder may be made to flow around the silver wire. After insertion into the co-axial structure the outside of the shaft can be heated to a temperature which causes the solder to flow inside the tube, thus mechanically connecting the silver wire to the inner e.g. copper wall of the tube.

FIG. 11(*c*) shows the arrangement of dielectric materials used in the matched structure. This drawing illustrates how the low permittivity PTFE dielectric 50 is impedance matched to the high permittivity tumour 70 using a transformer comprising of a dielectric material 60 with a relative permittivity value between that of the first dielectric material 50 and the third dielectric material 70 (calculated using equation 5), and of length that is an odd multiple of a quarter of the loaded wavelength at the frequency of interest (calculated using equation 4). It may be possible to use a dielectric material 60 that has a stepped permittivity profile where a plurality of dielectric materials are sandwiched together along the length of the transformer and each material is an odd multiple of a quarter of the wavelength of the EM wave inside the material at the frequency of interest.

In an alternative embodiment, the ring or swage is not present. Instead the outer conductor of the co-axial structure is crimped or otherwise pushed into the groove formed in the ceramic tip. This may be achieved using e.g. a pipe cutter positioned on the outside of the co-axial shaft such that the blade pushes the metal wall into the groove made in the ceramic tip.

The above two methods combine forming a second impedance transformer with securing the ceramic tip to the co-axial structure. The latter method is preferred over the soldering method as it provides a better reproducibility and yield.

Figure 12:
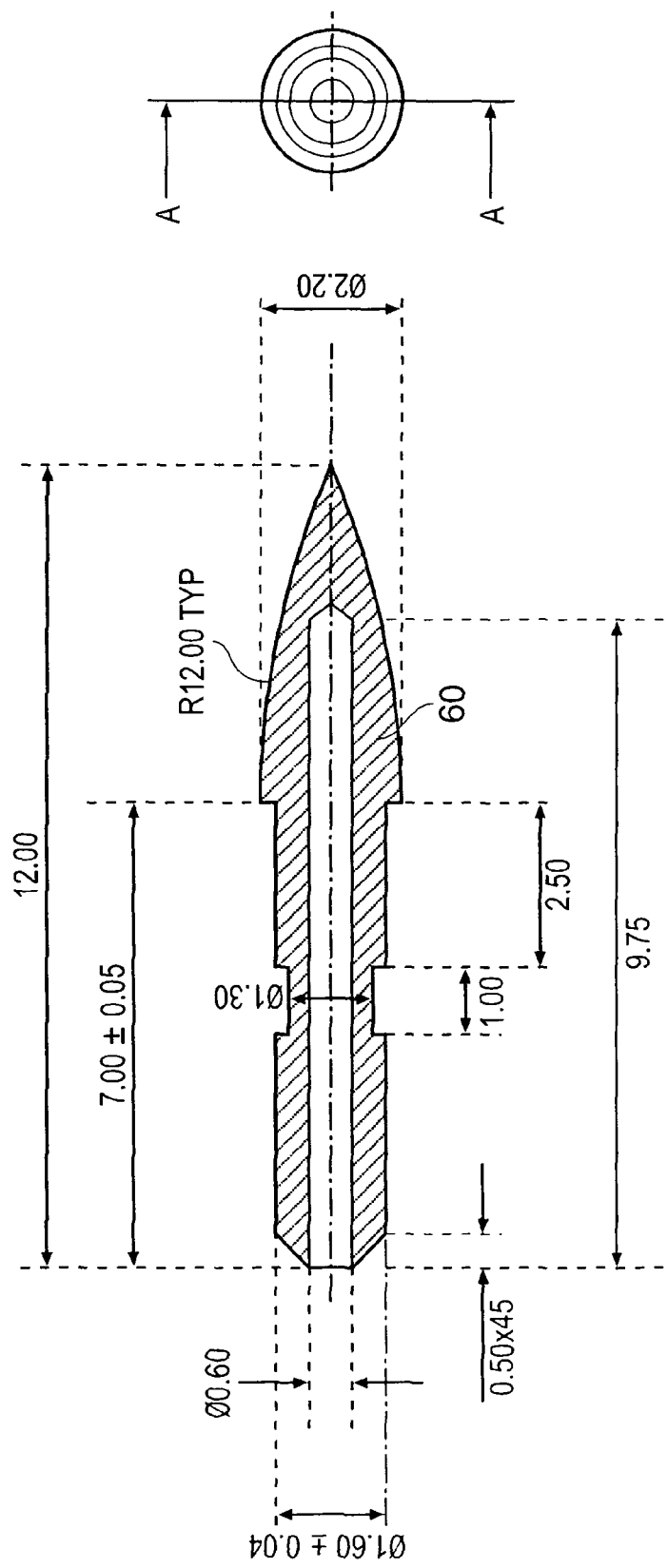
FIG. 12 is a dimensioned drawing of the ceramic tip part of the antenna shown in FIG. 11(a)

FIG. 12 shows a drawing for the ceramic tip matching transformer 60 with all of the dimensions necessary to manufacture the part. Suitable materials for the ceramic tip 60 include alumina and zirconia. Alumina is an engineering ceramic that offers good electrical insulation properties with high hardness and good wear resistance. Aluminas are generally white, but are sometimes pink or brown. It is possible to get a purity content of between 96% and 99.9%. Table 2 describes the properties of the alumina materials that can be used in the development of the antennas described in this specification.

TABLE 2

Properties of alumina ceramic and suppliers

| Manufacturer | Dielectric constant ($\epsilon_r$) | Dissipation factor (tanδ) | Purity (%) |
|---|---|---|---|
| mde<br>Persephonestraat 2<br>NL-5047 TT<br>Tilburg<br>The Netherlands<br>(www.mde.nl) | 9.8 | 0.0008 | 99.7 |
| Dynamic-Ceramic Ltd<br>Crewe Hall<br>Weston Road<br>Crewe<br>Cheshire UK<br>(www.Dynacer.com) | 9.0 | 0.00045 | Dynallox<br>99.7 |

The ceramic cone tip and matching circuit 60 may be machined and ground for the purpose of building prototype antennas, but it is preferable for a mould or a tool to be designed to enable large volume manufacture of these structures. The outer conductor 20 and the ceramic cone tip 60 may be coated with a biocompatible material 90, for example, Teflon or Parylene C may be used. It may be preferable to apply a conformal coating of the material 90 to enable ease of application.

It is preferable for the cone tip 60 to have a bend radius of around 12 mm to ensure that there is enough wall thickness between the centre conductor 30 and the ceramic material. It is not possible for the ceramic cone 60 to fit into the co-axial structure without air gaps being present between the two structures, therefore small air gaps were taken into account in the electromagnetic field simulations performed on the antenna structure. The end cone 60 could also be made from a number of flat surfaces with increasing angle towards the end of the tip. The general profile shown in FIGS. 11(a) and 11(b) should be followed and so it may be necessary to form the tip from a plurality of flat sections, for example, ten.

It may be preferable to use a solderless connector as the microwave connector connected to the proximal end of the antenna structure 10. A suitable candidate may be part number: 055-607-6702890, from the current range of ITT Cannon Precision SMA connectors. Since it is preferable for the outside layer of the outer conductor to be made from stainless steel, it is necessary to make a solder connection if a conventional SMA connector is to used. In this situation it is necessary to coat the stainless steel with a material that will enable this solder connection to be made effectively.

Measurement Aspect

In addition to enabling controlled tissue ablation to be performed from the distal tip of the antenna, the antenna structure must also allow for tissue impedances to be measured using reflected signal information provided by the antenna and dedicated electronic instrumentation designed to convert the reflected signal into amplitude and phase components. In the simulation results presented here, the impedances given are measured using a measurement port connected to the proximal end of the antenna structure.

Figure 13:
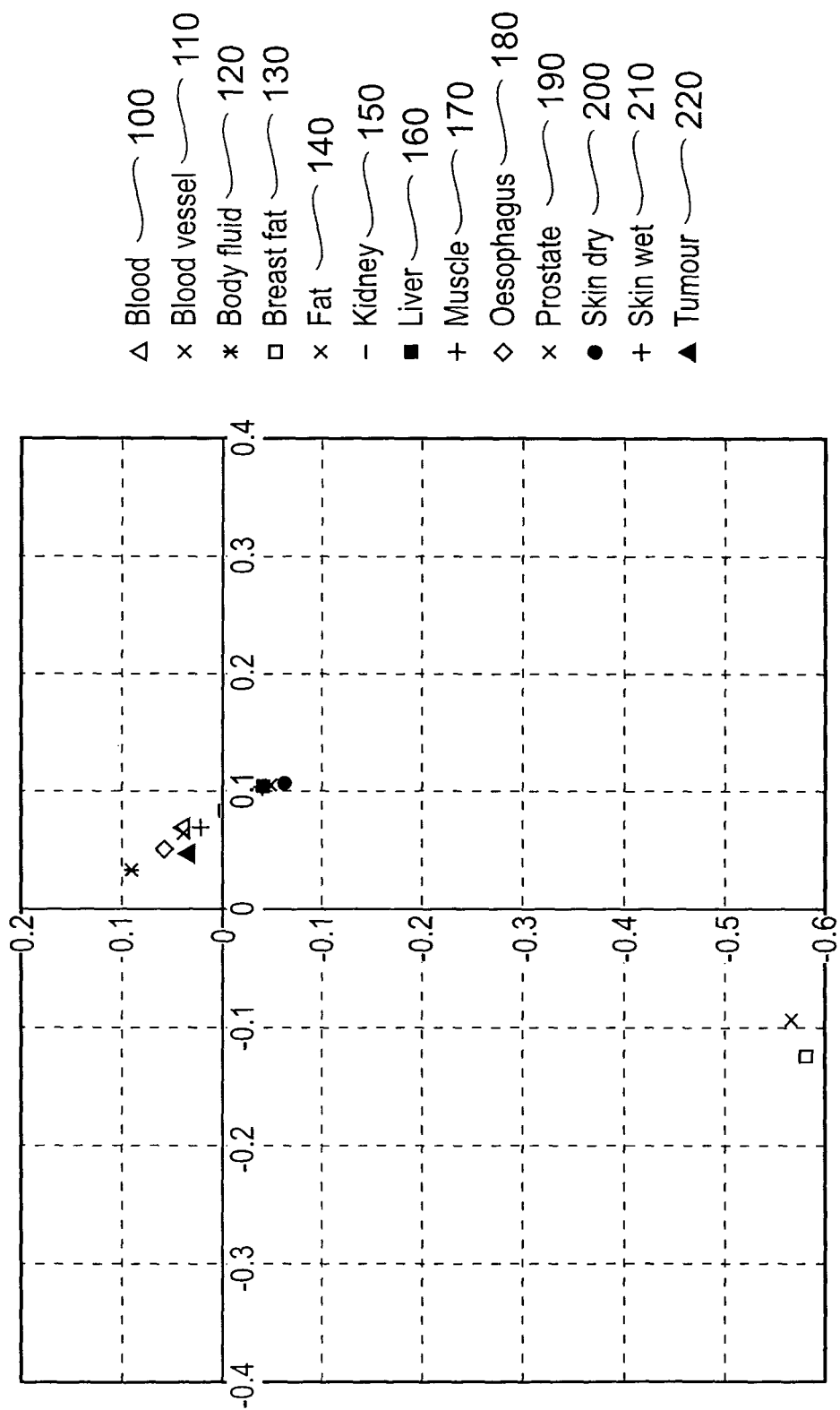
FIG. 13 is a Smith chart showing the detected impedance (reflection) points for a variety of materials.

FIG. 13 shows a plot of impedance values for various tissues. The results shown are measured at the proximal end of the antenna structure. Only a portion of the Smith chart is used to show the results. It can be seen that the reflections from the tissues given are clustered in two main groups. Reflections from general fat 140 and breast fat 130 are near the location (−0.1, −0.6), and those from other tissues are close to a line from (0.1, −0.5) to (0.25, 0.1). If the antenna impedance changed then it would not be expected that the clustering would change, but the points would move in unison, each point following a line that is an arc of a circle that passes through that point and two points diametrically opposite each other on the rim of the Smith chart (these two points would be (1,0) and (−1,0) if the phase reference was exactly at the junction between the antenna and the tissue). Because of the shape of these arcs, when the cluster is close to the centre of the Smith chart, the separation between individual points is the largest it can be. The effect of extra line length will be to rotate the points in unison around the centre of the chart, at (0,0). Attenuation in the co-axial structure will move the points fractionally closer to the centre of the Smith chart, for example, 1 dB of attenuation one way will result in the points moving 20% closer to the centre of the Smith chart, i.e. the picture will shrink by a factor of 0.8. The effect of phase changes (function of temperature or random flexure) will be to spread the points out into arcs around the centre. It is therefore important to use low loss co-axial cable with the lowest possible variation in phase due to temperature variation and random flexing. Table 3 shown below gives the complex impedances for the biological tissues corresponding to FIG. 13.

TABLE 3

Complex impedance for various materials at 14.5 GHz

| Medium | Real part (Ω) | Imaginary part (Ω) |
|---|---|---|
| Air | 23.43 | −j61.85 |
| Blood | 56.69 | +j4.80 |
| Blood vessel | 61.50 | −j5.85 |
| Body fluid | 52.20 | +j9.70 |
| Fat | 19.92 | −j35.80 |
| Kidney | 58.49 | +j0.37 |
| Liver | 60.85 | −j5.09 |
| Muscle | 56.88 | +j2.78 |
| Oesophagus | 54.60 | +j6.45 |
| Prostate | 56.23 | +j4.59 |
| Tumour | 54.39 | +j3.84 |

It can be seen from Table 3 that there is a significant difference in the complex impedance of fat 140 and tumour 220.

Figure 14:
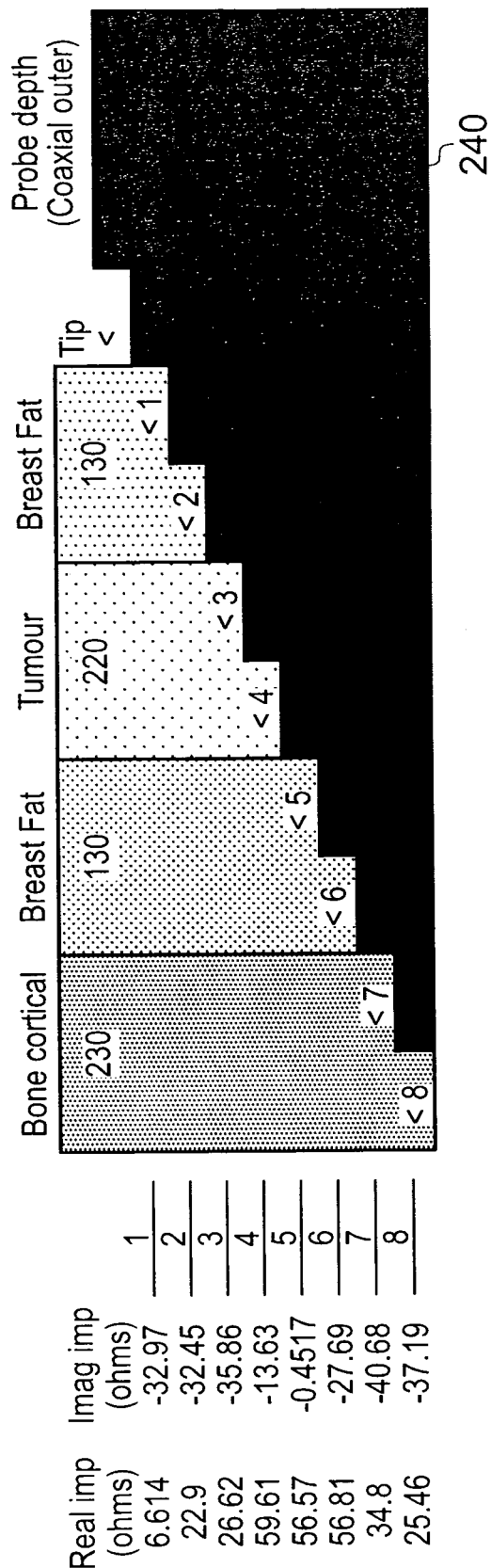
FIG. 14 illustrates schematically the movement of an antenna tip through various layers of different tissue types.
Figure 15:
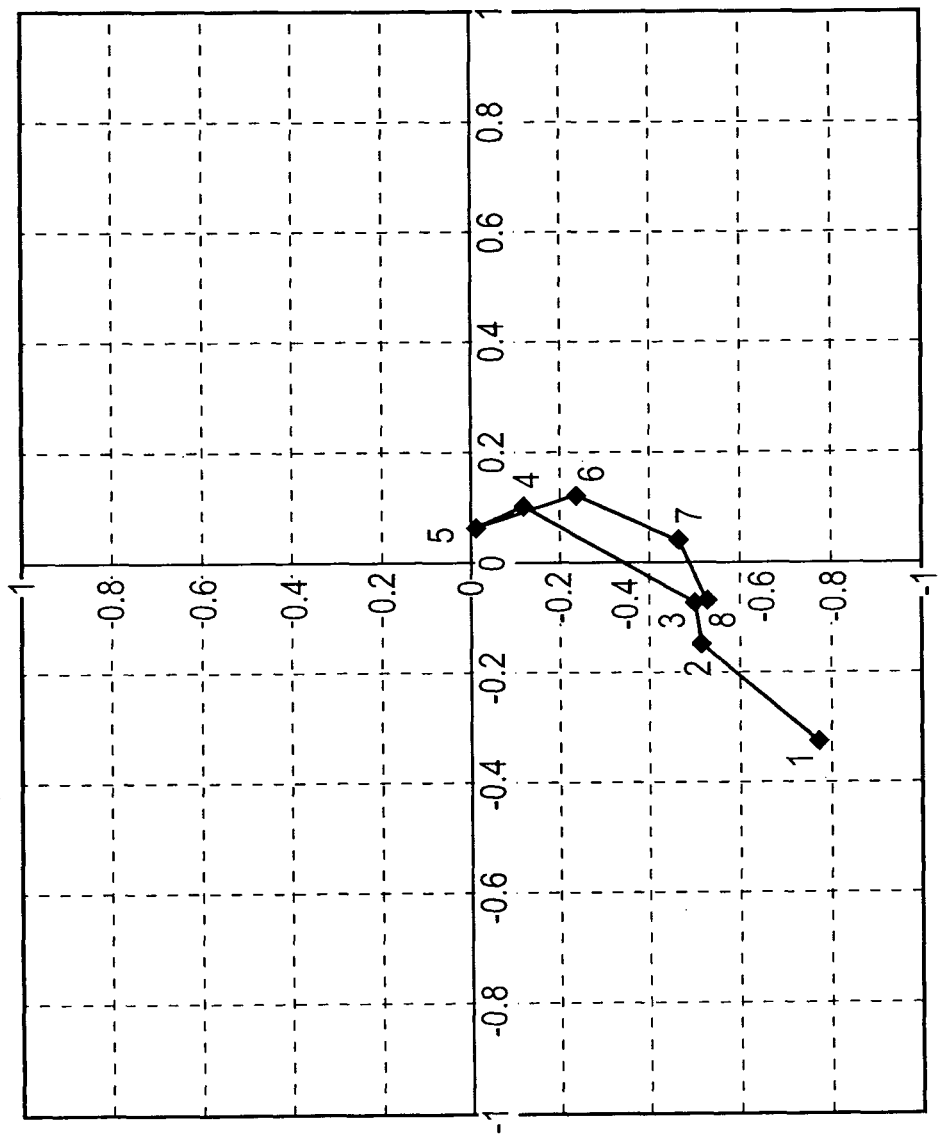
FIG. 15 is a Smith chart showing the locus of the impedance points detected by the antenna for the materials indicated in FIG. 14.

FIG. 14 shows the change in complex impedance as the distal tip of the antenna is inserted into various biological tissue structures. The black region 240 indicates the position of the tip into the layered medium. The tip is inserted in 5 mm steps, starting with the co-axial outer 20 located 5 mm from the outer breast fat layer 130—at this point the distal tip is just touching breast fat 130. It can be seen that there is a change in the real and imaginary parts of the complex impedance at the distal tip of the antenna as the antenna structure is pushed into the various layers of tissue. These results indicate that it will be possible to use the antenna described in this specification to differentiate between various tissue types, and, more importantly, it should be possible to use it to differentiate between normal and cancerous tissue. FIG. 15 shows the locus of impedance (reflection) as the distal tip of the antenna is inserted in 5 mm steps from air through 10 mm thick layers of breast fat 130, tumour 220 and bone cortical 230. It can be seen that none of the points on the locus sit on top of the other, hence it has been demonstrated that it is possible to differentiate between tissue types.

The simulations carried out in this work show significant differences between the magnitude and phase changes calculated from the reflections from the antenna, measured at the proximal end of the antenna structure, with the tip of the antenna in air, located inside fatty tissue, and also inside the tumour model. The results indicate that the antenna structure described in this work may be used to distinguish between various tissue types (or materials) located around the tip of the antenna by calculation of the amplitude and phase from the reflected signals measured at the proximal end of the antenna structure. It should be noted that the antenna structure described here and the measurement method described may enable various properties of other materials (biological and/or non-biological) to be measured.

Figure 16A:
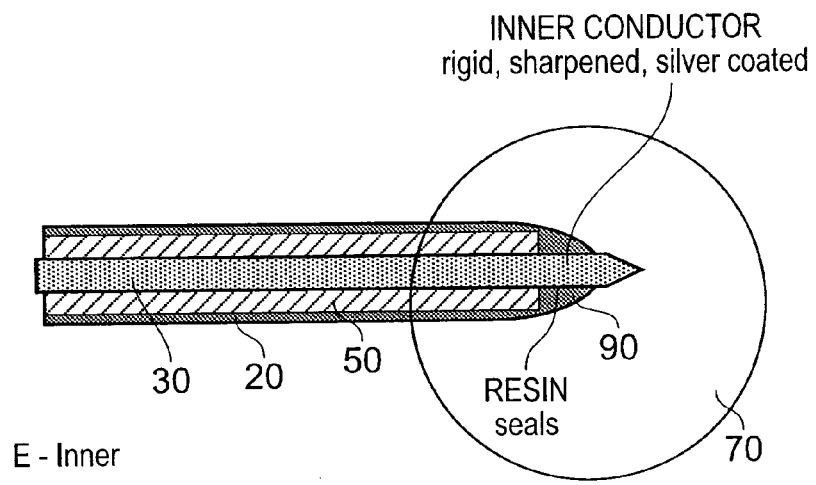
FIGS. 16(a) and 16(b) respectively show cross-section views of surgical antennas which are fifth and sixth embodiments of the present invention.
Figure 16B:
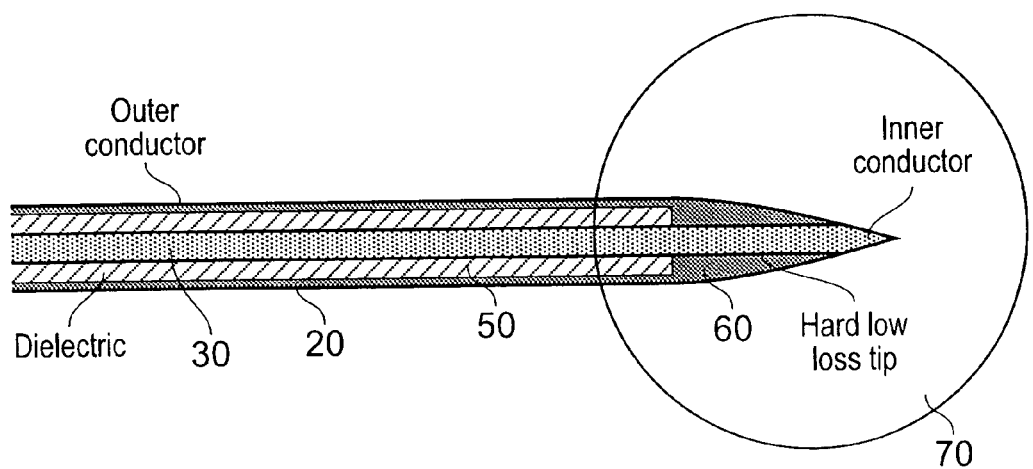

FIGS. 16(a) and 16(b) show alternative designs for the antenna structure described in this work. FIG. 16(a) shows a structure where the centre conductor 30 protrudes through a tip structure made from biocompatible material 90 (in this case, a resin), and the centre conductor 30 is in contact with tissue 70. In this structure, the centre conductor 30 comprises a rigid material that has been sharpened at the distal tip. It may be preferable for the centre conductor to be made from stainless steel, to provide the necessary rigidity and to make the structure biocompatible, and coated with a layer of silver to enable low loss propagation of the microwave signal. It is preferable for the thickness of the silver coating to be at least 5 skin depths, for example, around 10 μm of silver would be required at 14.5 GHz. It may be necessary to coat the overall structure with a second layer of biocompatible material, for example, Parylene C, to provide low friction between the antenna and the tissue and to ensure that the complete structure (co-axial cable and ceramic tip) is biocompatible. FIG. 16(b) shows a similar structure with a sharpened centre conductor 30 making contact with tissue 70. In this configuration, a hard ceramic material 60 is used to form the end section and enable the antenna structure to be pushed through tissue percutaneously. The hard ceramic should preferably be a low loss material and may exhibit a dielectric constant with a value between that of the first dielectric material 50 and the treatment tissue 70 to help provide impedance matching between the co-axial structure and the treatment tissue 70. It may be preferable (and required) for the complete structure to be coated with a conformal coating of a biocompatible material, for example, a 10 μm layer of Parylene C.

Figure 18A:
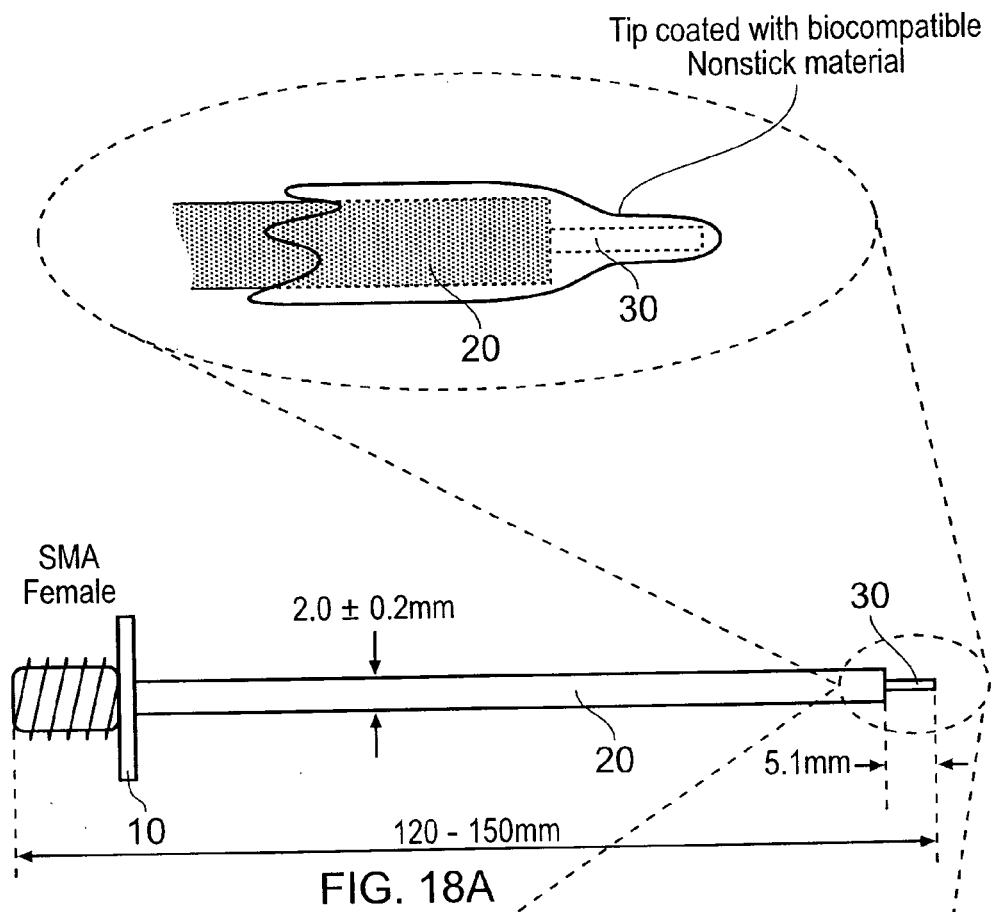
FIGS. 18(a) and 18(b) show a surgical antenna which is an eighth embodiment of the present invention, FIG. 18(a) showing the complete antenna and a cross-section of the tip, and FIG. 18(b) showing a cross-section looking down the antenna axis.
Figure 18B:
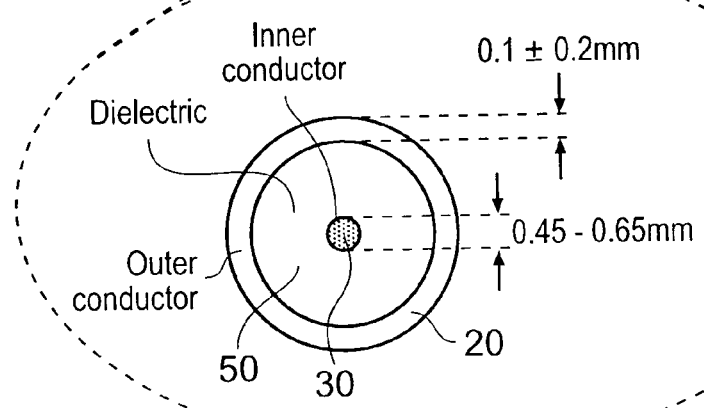

FIGS. 17(a), 17(b) and 17(c) show a simple monopole antenna using a rigid co-axial cable coated with a layer of biocompatible material 90. FIG. 17(a) shows the overall assembly, where the outer diameter of the outer conductor 20 is 3.0 mm and the proximal end of the antenna is terminated with an SMA female connector. FIG. 17(b) shows the cross section of the co-axial antenna from the distal tip; each of the components in the structure is labelled. FIG. 17(c) shows a specific embodiment with dimensions. FIGS. 18(a) and 18(b) show a similar arrangement where the outside diameter of the outer conductor 20 is reduced to 2.0 mm and the biocompatible material covers the monopole section of the centre conductor 30 and a region of the outer conductor 20.

The invention claimed is:

1. A surgical antenna for insertion into tissue, the antenna comprising:
    an elongated body with an inner conductor along its length, an outer conductor surrounding the inner conductor and separated therefrom by a dielectric material,
    a connector for connecting the inner conductor and the outer conductor to a microwave power source to receive microwave frequency energy therefrom, and
    an insertion tip at a distal end of the elongated body for penetrating the tissue, the insertion tip having an impedance at the microwave frequency that is different from an impedance at the proximal end of the antenna,
    wherein the insertion tip comprises an independent piece of dielectric material configured to both act as a first impedance transformer to match the dielectric material of the elongated body with the tissue at the microwave frequency and to penetrate the tissue, and
    wherein the elongated body includes a second impedance transformer arranged to introduce a capacitive or inductive reactance into the antenna.

2. A surgical antenna according to claim 1, wherein the insertion tip is made from material that is independent of the dielectric material of the elongated body and has a dielectric constant value between that of the dielectric material of the elongated body and that of the tissue.

3. A surgical antenna according to claim 2, wherein the dielectric constant value of the insertion tip increases towards its distal end.

4. A surgical antenna according to claim 1, wherein the independent piece of dielectric material comprises a ceramic which exhibits low loss at the microwave frequency.

5. A surgical antenna according to claim 4, wherein the ceramic is alumina or zirconia.

6. A surgical antenna according to claim 2, wherein the inner conductor extends into the insertion tip beyond the axial extent of the outer conductor, the insertion tip thereby being an omnidirectional aerial.

7. A surgical antenna according to claim 1, wherein the outer conductor is cylindrical and coaxial with the inner conductor.

8. A surgical antenna according to claim 1, wherein the second impedance transformer comprises a fixed tuning stub arranged to introduce an inductive or capacitive reactance.

9. A surgical antenna according to claim 1, wherein the second impedance transformer is a narrowed portion of the outer conductor of the elongated body received in a groove formed in the insertion tip.

10. A surgical antenna according to claim 9, wherein the insertion tip is securely gripped by the elongated body at the narrowed portion.

11. A surgical antenna according to claim 1, wherein the second impedance transformer includes a metal ring received in a groove formed in the insertion tip.

12. A surgical antenna according to claim 11, wherein the metal ring is made from silver.

13. A surgical antenna according to claim 11, wherein the outer conductor is attached to the metal ring to secure the insertion tip to the elongated body.

14. A surgical antenna according to claim 13, wherein the inner surface of the outer conductor is soldered to the metal ring.

15. A surgical antenna according to claim 1, wherein the first and/or second impedance transformers are quarter wavelength impedance transformers.

16. A surgical antenna according to claim 1, having a distal insertable portion including the insertion tip with a diameter of 2.2 mm, the insertion portion being suitable for insertion percutaneously inside the human body.

17. A surgical antenna according to claim 16, wherein the insertable portion is receivable in an endoscope.

18. A surgical antenna according to claim 16, wherein the insertion tip has a sharp distal point.

19. A surgical antenna according to claim 16, wherein the insertion tip has a biocompatible coating.

20. A surgical antenna according to claim 1, wherein the microwave frequency is in the range 5-60 GHz.

21. A surgical antenna according to claim 1, contained in a sterile package as a disposable item.

22. A tissue treatment apparatus for delivering microwave frequency energy to biological tissue, the apparatus including:
    a microwave power source;
    a surgical antenna comprising:
    an elongated body with an inner conductor along a length thereof,
    an outer conductor surrounding the inner conductor and separated therefrom by a dielectric material,
    a connector connecting the inner conductor and the outer conductor to the microwave power source to receive microwave frequency energy from the microwave power source, and
    an insertion tip at a distal end of the elongated body, the insertion tip comprising an independent piece of dielectric material having an impedance at the microwave frequency that is different from an impedance at the proximal end of the antenna, wherein the insertion tip is configured to both act as a first impedance transformer to match the dielectric material of the elongated body with the tissue at the microwave frequency to radiate microwave energy from the distal insertion tip and to penetrate into the biological tissue; and a tuning filter arranged to dynamically match an impedance of the source to an impedance of a tissue load at the distal insertion tip, wherein the elongated body of the surgical antenna includes a second impedance transformer arranged to introduce a capacitive or inductive reactance into the surgical antenna.

* * * * *